United States Patent [19]

Egawa et al.

[11] Patent Number: 5,399,631
[45] Date of Patent: Mar. 21, 1995

[54] POLYVINYL ETHER COMPOUND

[75] Inventors: Tatsuya Egawa; Yasuhiro Kawaguchi; Kenji Mogami; Nobuaki Shimizu, all of Sodegaura, Japan

[73] Assignee: Idemitsu Kosan Co., Ltd., Tokyo, Japan

[21] Appl. No.: 66,238

[22] Filed: May 25, 1993

[30] Foreign Application Priority Data

Jun. 4, 1992 [JP] Japan .................................. 4-143922
Sep. 7, 1992 [JP] Japan .................................. 4-237842

[51] Int. Cl.$^6$ .................... C08F 116/70; C08F 116/18
[52] U.S. Cl. ................. 525/328.9; 568/672; 526/332; 526/333; 525/940
[58] Field of Search ............... 526/332, 333; 525/328.9, 940; 568/672

[56] References Cited

U.S. PATENT DOCUMENTS 2,104,000 12/1937 Reppe et al. ...................... 526/90
3,085,997 4/1963 Martin ............................. 526/332 X
5,196,491 3/1993 Cho et al. ....................... 526/185
5,272,233 12/1993 Crivello et al. .................. 526/279

OTHER PUBLICATIONS

Higashimura, T et al. (1988) Polymer Preprints 29(2), 1-2.

Primary Examiner—Mark Nagumo
Attorney, Agent, or Firm—Antonelli, Terry, Stout & Kraus

[57] ABSTRACT

A method of production of an ether compound from an acetal compound or a ketal compound which is excellent in conversion and selectivity and does not cause corrosion of apparatuses and a novel useful polyvinyl ether compound as lubricating oil for compression-type refrigerators, electric insulation oil and the like are disclosed. The method of production of the present invention comprises reaction of an acetal compound or a ketal compound with hydrogen in the presence of a solid catalyst having acidic property and hydrogenation ability to produce the corresponding ether compound. The polyvinyl ether compound of the present invention comprises the constituting unit expressed by the general formula:

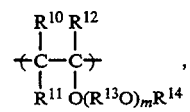

(characters in the general formula are the same as those described in the specification), contains none of unsaturated bond, acetal structure and aldehyde structure in the molecule and has weight average molecular weight in the range of 300 to 3000.

5 Claims, 30 Drawing Sheets

POLYVINYL ETHER COMPOUND

BACKGROUND OF THE INVENTION

1. Field of the Invention

The present invention is related to a novel method of producing an ether compound and to a novel polyvinyl ether compound. More particularly, the present invention is related to a method of efficiently producing a useful ether compound having a wide range of applications as solvent, lubricating oil and the like by hydrogenation of an acetal compound or a ketal compound and a novel polyvinyl ether compound useful as lubricating oil for compression-type refrigerators, electric insulation oil, organic solvent, surface active agent and the like.

2. Description of the Related Arts

As the method of producing an ether compound from acetal compounds or ketal compounds, for example, a method of using a combination of an acid and an alkali metal hydride, a method of using a silicon reagent and a method of using diborane or the like are shown in "Jikken Kagaku Koza", Volume 20, the 4th edition (published by Maruzen). However, these reactions use stoichiometric amounts of very expensive materials like the alkali metal hydride, diborane and the silicon reagent as the hydrogenating reagent and are not preferable as the method of industrial production.

A method of a combination of an acid catalyst and catalytic hydrogenation is known. W. L. Howard [J. Org. Chem. Volume 26, Page 1026 (1961)] reported formation of an ether by catalytic hydrocracking of a ketal by using a catalyst in which rhodium is supported on alumina in the presence of hydrochloric acid. In the specification of the U.S. Pat. No. 4,088,700, a method of production of an ether compound by catalytic hydrocracking of 1,3-dioxoranes which are cyclic acetals by using a platinum catalyst or a rhodium catalyst in the presence of a Lewis acid such as boron trifluoride, aluminum trichloride and the like is shown. However, because these methods of production use hydrochloric acid, boron trifluoride, aluminum trichloride and the like, corrosion of the apparatus becomes the problem when the ordinary apparatus is used and a special treatment is necessary, making the method unfavorable.

As the method without using acids, for example, methods of producing an ether compound by hydrocracking of acetals by a palladium catalyst supported on carbon were proposed in Japanese Patent Application Laid Open No. 1983-4739 and Japanese Patent Application Laid Open No. 1983-177929. Though these methods do not have the problem of corrosion of apparatus because they do not use acids, conversion of the material acetal is not satisfactory. In these methods, a processes for separating the product and the materials from each other and recycling the materials is necessary and this is not preferable. Furthermore, when the ether formed cannot be separated and purified by distillation or the like, the acetal is left in the product. Because acetals in general are lacking in stability, particularly in resistance to hydrolysis, aldehydes formed from them have oxidation, reduction, polycondensation and the like reactions to cause problem of deterioration of properties of the product to a great extent. Thus, the range of application of these methods is inevitably very limited.

Thus, a method of production of the ether compound from an acetal compound or a ketal compound which has sufficient reaction activity, shows good selectivity and does not cause corrosion of the apparatus has not been discovered yet and development of such a method is strongly desired.

Compression-type refrigerators are generally constituted with a compressor, a condenser, an expansion valve and an evaporator and has a structure that mixed fluid of refrigerant and lubricating oil is circulated in this closed system. In the compression-type refrigerator, generally temperature is 50° C. or higher in the compressor and about −40° C. or lower in the refrigerating chamber although the temperature is different depending on kind of apparatus and it is generally required that the refrigerant and the lubricating oil are circulated in the system without causing phase separation in the range of temperature of −40° C. to +50° C. When the phase separation occurs during the operation of the refrigerator, life and efficiency of the apparatus are adversely affected to a great extent. For example, when the phase separation of the refrigerant and the lubricating oil occurs in the part of the compressor, lubrication of the moving parts is deteriorated and seizure occurs to cause decrease of life of the apparatus to a great extent. When the phase separation occurs in the evaporator, efficiency of heat exchange is decreased because of the presence of lubricating oil of high viscosity.

Because the lubricating oil for refrigerators is used for the purpose of lubricating moving parts in refrigerators, the lubricating property is naturally important. Particularly, because the temperature in the compressor is high, the viscosity which can hold the oil film necessary for the lubrication is important. The required viscosity is different depending on the kind of the compressor used and conditions of use and it is generally preferable that viscosity (kinematic viscosity) of the lubricating oil before mixing with the refrigerant is 5 to 1000 cSt at 40° C. When the viscosity is lower than this range, oil film becomes thin to cause insufficient lubrication, and, when the viscosity is higher than this range, the efficiency of the heat exchange is decreased.

Electric refrigerators have the motor and the compressor built into a single body and lubricating oil for them is required to have a high degree of electric insulating property. In general, a volume specific resistance of $10^{12}$ Ω.cm or more at 80° C. is required. When the resistance is lower than this value, possibility of leak of electricity arises.

As the refrigerant for compressor-type refrigerators, mainly dichlorodifluoromethane (referred to as Flon 12 hereinafter) has heretofore been used and, as the lubricating oil, various kinds of mineral oil and synthetic oil satisfying the required properties described above have been used. However, chlorofluorocarbons (CFC) including Flon 12 are being more rigorously restricted world-wide because they cause environmental pollution such as the rupture of the ozone layer. By this reason, hydrogen-containing Flon compounds such as hydrofluorocarbons (HFC) and hydrochlorofluorocarbons (HCFC) are attracting attention as the novel kinds of the refrigerant. The term Flon compound described above and hereinafter stands for a chlorofluorocarbon, a hydrofluorocarbon and a hydrochlorofluorocarbon in general. The hydrogen-containing fluorocarbons, particularly hydrofluorocarbons (HFC) represented by 1,1,1,2-tetrafluoroethane (referred to as Flon 134a hereinafter), are preferred as the refrigerant for compression-type refrigerators because they have little possibility of causing the rupture of the ozone layer and can replace Flon 12 with little change of the structure of refrigerators which have heretofore been used.

When a hydrogen-containing Flon compound described above, such as Flon 134a and the like, is adopted as the refrigerant for compression-type refrigerators to replace Flon 12, a lubricating oil having good compatibility with the hydrogen-containing Flon compound, such as Flon 134a and the like, and good lubricating property satisfying the requirements described above is naturally required. However, because the lubricating oils used in combination with Flon 12 heretofore do not have good compatibility with the hydrogen-containing Flon, such as Flon 134a and the like, a new lubricating oil suited for these compounds is required. When a new lubricating oil is adopted in accordance with replacement of Flon 12, it is desired that major change of the structure of the apparatus is not necessary. It is not desirable that the structure of the currently used apparatus must have major changes because of a lubricating oil.

As the lubricating oil having the compatibility with Flon 134a, for example, lubricating oils of polyoxyalkylene glycols have been known. For example, Research Disclosure No. 17463 (October, 1978), the specification of the U.S. Pat. No. 4,755,316, Japanese Patent Application Laid Open No. 1989-256594, Japanese Patent Application Laid Open No. 1989-259093, Japanese Patent Application Laid Open No. 1989-259094, Japanese Patent Application Laid Open No. 1989-271491, Japanese Patent Application Laid Open No. 1990-43290, Japanese Patent Application Laid Open No. 1990-84491, Japanese Patent Applications Laid Open No. 1990-132176 to 132178, Japanese Patent Application Laid Open No. 1990-132179, Japanese Patent Application Laid Open No. 1990-173195, Japanese Patent Applications Laid Open No. 1990-180986 to 180987, Japanese Patent Applications Laid Open No. 1990-182780 to 182781, Japanese Patent Application Laid Open No. 1990-242888, Japanese Patent Application Laid Open No. 1990-258895, Japanese Patent Application Laid Open No. 1990-269195, Japanese Patent Application Laid Open No. 1990-272097, Japanese Patent Application Laid Open No. 1990-305893, Japanese Patent Application Laid Open No. 1991-28296, Japanese Patent Application Laid Open No. 1991-33193, Japanese Patent Applications Laid Open No. 1991-103496 to 103497, Japanese Patent Application Laid Open No. 1991-50297, Japanese Patent Application Laid Open No. 1991-52995, Japanese Patent Applications Laid Open No. 1991-70794 to 70795, Japanese Patent Application Laid Open No. 1991-79696, Japanese Patent Application Laid Open No. 1991-106992, Japanese Patent Application Laid Open No. 1991-109492, Japanese Patent Application Laid Open No. 1991-121195, Japanese Patent Application Laid Open No. 1991-205492, Japanese Patent Application Laid Open No. 1991-231992, Japanese Patent Application Laid Open No. 1991-231994, Japanese Patent Application Laid Open No. 1992-15295, Japanese Patent Application Laid Open No. 1992-39394 and Japanese Patent Applications Laid Open No. 1992-41591 to 41592 disclosed such lubricating oils. However, the lubricating oils of polyoxyalkylene glycols generally have low volume specific resistances and no example satisfying the value of $10^{12}$ $\Omega$.cm or more at 80° C. has been disclosed yet.

As the compound having the compatibility with Flon 134a in addition to the lubricating oils of polyoxyalkylene glycols, lubricating oils of esters were disclosed in British Patent Laid Open No. 2216541, WO No. 6979 (1990), Japanese Patent Applications Laid Open No. 1990-276894, Japanese Patent Applications Laid Open No. 1991-128992, Japanese Patent Applications Laid Open No. 1991-88892, Japanese Patent Applications Laid Open No. 1991-179091, Japanese Patent Applications Laid Open No. 1991-252497, Japanese Patent Applications Laid Open No. 1991-275799, Japanese Patent Applications Laid Open No. 1992-4294, Japanese Patent Applications Laid Open No. 1992-20597 and the specification of the U.S. Pat. No. 5,021,179. However, it is inevitable because of the structural characteristic that carboxylic acids are formed by hydrolysis of the lubricating oils of esters.

Lubricating oils of carbonates were disclosed in Japanese Patent Application Laid Open No. 1991-149295, European Patent No. 421298, Japanese Patent Application Laid Open No. 1991-217495, Japanese Patent Application Laid Open No. 1991-247695, Japanese Patent Application Laid Open No. 1992-18490 and Japanese Patent Application Laid Open No. 1992-63893. However, the lubricating oils of carbonates have the same problem of hydrolysis as the lubricating oils of esters.

Thus, it is the real situation at present that a lubricating oil for the compression-type refrigerators having excellent compatibility with Flon 134a, excellent stability and lubricating property and a volume specific resistance at 80° C. of $10^{12}$ $\Omega$.cm or more has not been discovered yet. Development of such a lubricant is strongly desired.

Concerning generally known polyalkyl vinyl ethers, examples of synthesis of various kinds of alkyl polyvinyl ether are described in "Jikken Kagaku Koza", Volume 18, "Reaction of organic compounds II(A)", edited by Chemical Society of Japan (published by Maruzen). Ends of these polymers are olefins in the case of the acid catalysts and acetals when an alcohol is present in addition to the acid catalyst. When water is present, ends of acetal and ends of aldehyde are also formed. The end of olefin causes coloring and increase of viscosity in the presence of an acid and the end of aldehyde also causes coloring. Acetals are decomposed to olefins and alcohols in the presence of an acid. The olefins react with each other to cause coloring and increase of viscosity and, when water is present additionally, aldehydes are formed, also causing coloring. However, a polyvinyl ether compound which does not contain these structures causing degradation, such as the structures of acetals, aldehydes and olefins, at the end of the molecule has not been reported yet.

SUMMARY OF THE INVENTION

The present invention has an object of providing a method of efficiently producing an ether compound having a wide range of applications as solvent, lubricating oil and the like by hydrogenation of an acetal compound or a ketal compound by using a catalyst having a sufficient reaction activity and excellent selectivity and causing no corrosion of the apparatus. The present invention has another object of providing a novel polyvinyl ether compound favorably utilized particularly as the lubricating oil for compression-type refrigerators having sufficient compatibility with hydrogen-containing Flon compounds, such as Flon 134a, excellent stability and lubricating property and a volume specific resistance at 80° C. of $10^{12}$ Ω.cm or more.

As the result of the intensive studies by the present inventors for achieving the first object described above, it was discovered that the object can be achieved by using a solid catalyst having acidic property and hydrogenating ability as the catalyst. Furthermore, as the result of the intensive studies for achieving the second object of the present invention, it was discovered that the object can achieved by a polymer of an alkyl vinyl ether of a specific structure which does not contain any of an unsaturated bond, an acetal structure and an aldehyde structure and has the weight average molecular weight in a specific range. The present invention was completed on the basis of these discoveries.

Thus, the first of the present invention provides a method of production of an ether compound expressed by the general formula (II) or (III):

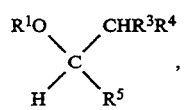

(II)

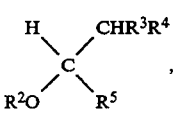

(III)

wherein $R^1$ and $R^2$ are a hydrocarbon group or a hydrocarbon group containing ether oxygens in the main chain, in the side chain or in the both of them, respectively, and may be the same or different from each other and $R^3$, $R^4$ and $R^5$ are a hydrogen atom, a hydrocarbon group or a hydrocarbon group containing ether oxygens in the main chain, in the side chain or in the both of them, respectively, and may be the same or different from each other, comprising bringing an acetal compound or a ketal compound expressed by the general formula (I):

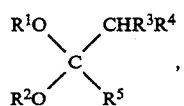

(I)

wherein $R^1$, $R^2$, $R^3$, $R^4$ and $R^5$ are the same as those in the general formulae (II) and (III), into the reaction with hydrogen in the presence of a solid catalyst having acidic property and hydrogenating ability.

The second of the present invention provides a polyvinyl ether compound comprising constituting units expressed by the general formula (IX):

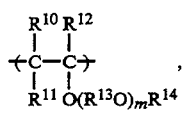

(IX)

wherein $R^{10}$, $R^{11}$ and $R^{12}$ are a hydrogen atom or an alkyl group having 1 to 4 carbon atoms, respectively, and may be the same or different from each other, $R^{13}$ is an alkylene group having 2 to 4 carbon atoms, $R^{14}$ is an alkyl group having 1 to 10 carbon atoms, m is a number the average of which is in the range of 0 to 10, $R^{10}$ to $R^{14}$ may be the same or different between the constituting units and a plural of $R^{13}O$'s may be the same or different from each other when the constituting unit contains a plural of $R^{13}O$'s, does not contain any of an unsaturated bond, an acetal structure and an aldehyde structure in the molecule and has a weight average molecular weight of 300 to 3000.

DESCRIPTION OF PREFERRED EMBODIMENTS

Figure 1:
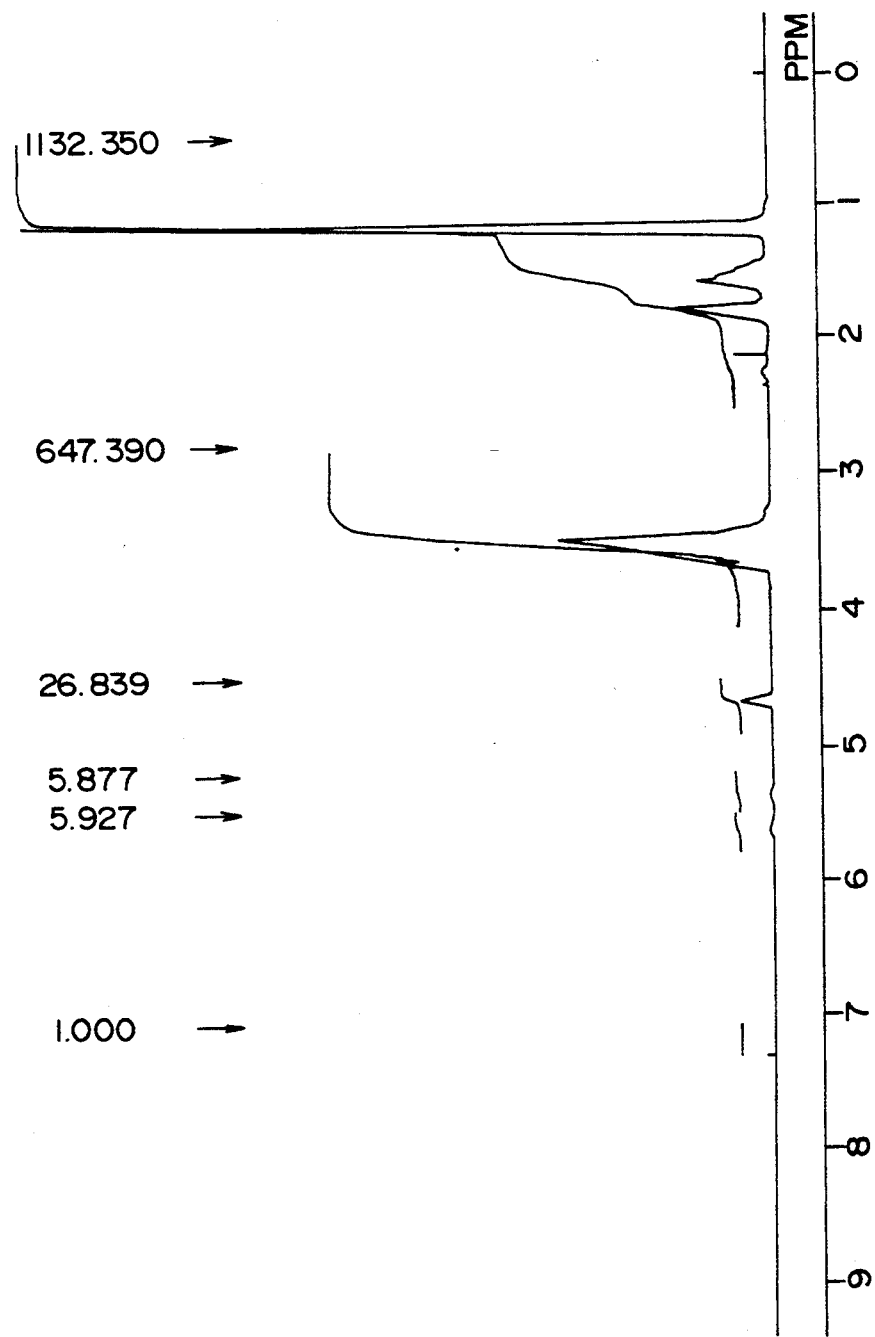
FIG. 1 and FIG. 2 are a $^1$H-NMR chart of the acetal oligomer produced in Example 3 (1) and a $^1$H-NMR chart of the ether compound produced in Example 3 (2), respectively.

The ether compound of the first object of the present invention is described first.

In the method of production of an ether compound of the present invention, an acetal compound or a ketal compound expressed by the general formula (I):

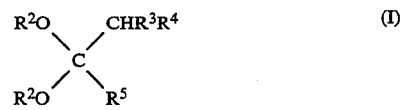

(I)

is used as the starting material. In the general formula (I), $R^1$ and $R^2$ are, respectively, a hydrocarbon group such as methyl group, ethyl group, n-propyl group, isopropyl group and the like, or a hydrocarbon group containing ether oxygens in the main chain, in the side chain or in the both of them, such as the groups expressed by the general formulae:

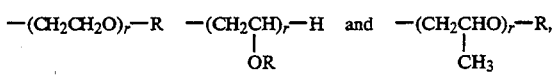

wherein R is a hydrocarbon group having 1 to 10 carbon atoms and r is an integer of 1 to 500. $R^1$ and $R^2$ may be the same or different from each other. $R^3$, $R^4$ and $R^5$ are a hydrogen atom, a hydrocarbon group or a hydrocarbon group containing ether oxygens in the main chain, in the side chain or in the both of them, respectively. Examples of the hydrocarbon group or the hydrocarbon group containing ether oxygens are the same groups as those shown as examples in the description of $R^1$ and $R^2$ and groups expressed by the general formula:

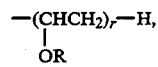

wherein R and r are the same as those described above. $R^3$, $R^4$ and $R^5$ may be the same or different from each other.

In the present invention, an ether compound expressed by the general formula (II) or (III):

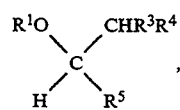 (II)

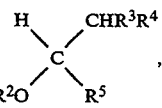 (III)

wherein $R^1$, $R^2$, $R^3$, $R^4$ and $R^5$ are the same as those described above, is obtained by the reaction of the acetal compound or the ketal compound expressed by the general formula (I) with hydrogen in the presence of a solid catalyst having acidic property and hydrogenating ability.

As the acetal compound or the ketal compound expressed by the general formula (I), a compound expressed by the general formula (IV):

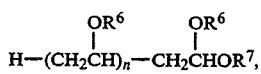 (IV)

wherein $R^6$ and $R^7$ are a hydrocarbon group having 1 to 20 carbon atoms or a hydrocarbon group containing ether oxygens, respectively, and may be the same or different from each other, $R^6$ is the same or different between the constituting units and n is an integer of 1 to 500, is preferred and, in this case, a compound expressed by the general formula (V) or (VI):

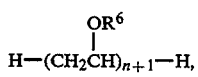 (V)

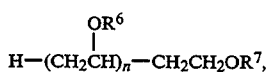 (VI)

wherein $R^6$, $R^7$ and n are the same as those described above, is obtained as the ether compound.

In the compound expressed by the general formula (IV), a compound expressed by the general formula (XIV):

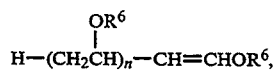 (XIV)

wherein $R^6$ and n are the same as those describe above, is occasionally contained. When a mixture like this is used, the ether compound obtained is the compound expressed by the general formula (V) described above or a mixture of the compound expressed by the general formula (V) and the compound expressed by the general formula (VI).

As the acetal compound and the ketal compound expressed by the general formula (I), a compound expressed by the general formula (VII):

$$R^8CH(OR^9)_2 \quad (VII),$$

wherein $R^8$ and $R^9$ are a hydrocarbon group having 1 to 20 carbon atoms, respectively, and may the same or different from each other, is also favorably used. In this case, a compound expressed by the general formula (VIII):

$$R^8CH_2OR^9 \quad (VIII)$$

wherein $R^8$ and $R^9$ are the same as those described above, is obtained as the ether compound.

In the method of the present invention, a solid catalyst having acidic property and hydrogenating ability is utilized. As the solid catalyst having acidic property and hydrogenating ability, either a combination of two kinds of catalyst which are a hydrogenation catalyst and a solid acid catalyst or a solid acid catalyst having hydrogenating ability is utilized.

The hydrogenation catalyst is not particularly limited and various kinds of generally used hydrogenation catalyst can be utilized. For example, (1) catalysts of an elementary metal like nickel, palladium, rhodium, platinum, ruthenium and the like and catalysts containing these metals as the main components, (2) catalysts having the metal catalyst component of (1) supported on activated charcoal, alumina, diatomaceous earth or the like and (3) Raney catalysts like Raney nickel, Raney cobalt and the like are particularly effective.

The solid acid catalyst is not particularly limited and various kinds of generally used solid acid catalyst can be used. For example, activated clay, acidic clay, various kinds of zeolite, ion exchange resins, silica-alumina, heteropolyacids and the like are particularly effective.

The solid acid catalyst having hydrogenating ability is not particularly limited and various kinds of generally used solid acid catalyst having hydrogenating ability can be used. For example, catalysts in which nickel, palladium, rhodium, platinum, ruthenium or the like is supported on various kinds of zeolite are particularly effective.

The amount of the catalyst preferable for performing the method of the present invention is as following. When the combined catalyst is used, the amount of the hydrogenation catalyst is 0.1 to 50 weight % and the amount of the solid catalyst is 0.1 to 50 weight % based on the amount of the reacting materials, respectively. When the solid acid catalyst having the hydrogenating ability is used, the amount is 0.1 to 50 weight % based on the amount of the reacting materials. When the amount is less than 0.1 weight %, the reaction does not proceed sufficiently. When the amount is more than 50 weight %, the amount of the catalyst based on the amount of the reacting materials is too much and the problem of decrease of the productivity arises.

In the present invention, the acetal compound or the ketal compound expressed by the general formula (I) is brought into reaction with hydrogen in the presence of the catalyst described above. It is preferable that hydrogen gas and the acetal compound or the ketal compound are brought into contact with each other in the mol ratio of 1:10 to 200:1. When the mol ratio is less than the specified range, the reaction does not proceed sufficiently. When the mol ratio is more than the specified range, the problem of decrease of the productivity arises.

The preferred conditions of the reaction for performing the reaction by the method of the present invention are: the reaction temperature, 10° to 250° C.; the partial pressure of hydrogen, 1 to 200 kg/cm²; the time of reaction in the case of the batch reaction, 0.1 to 10 hours; and in the case of the reaction in the liquid flow system, the weight space velocity (WHSV) of the reacting fluid, 0.01 to 100/hour; and the gas space velocity (GHSV) of hydrogen gas, 100 to 10000/hour.

The reaction can be performed without a solvent but a solvent may be used when the solvent is stable at the reaction conditions. Examples of the solvents which can be used are hydrocarbon solvents, such as hexane, heptane, octane and the like.

By the reaction described above, $-OR^1$ group or $-OR^2$ group which constitutes a part of the acetal compound or the ketal compound expressed by the general formula (I) is eliminated from the acetal compound or the ketal compound and replaced with a hydrogen to form the ether compound expressed by the general formula (II) or the general formula (III). In this reaction, it was made clear that, when any of $R^1$ to $R^5$ is a hydrocarbon group containing ether oxygens, hydrogen does not react with the ether oxygen but reacts with the oxygen in the part of the acetal or the ketal alone.

After the reaction is finished, the reaction product can be separated from the catalyst by the ordinary filtration or decantation. The catalyst separated here can be used again without particular treatment.

The reaction product may be formed into the product through processes like distillation, extraction, washing, drying and the like according to necessity.

The novel polyvinyl ether compound as the second object of the present invention is described in the following.

The polyvinyl ether compounds of the present invention comprises the constituting units expressed by the general formula (IX):

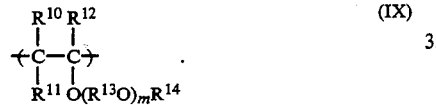

In the general formula (IX) described above, $R^{10}$, $R^{11}$ and $R^{12}$ are a hydrogen atom or an alkyl group having 1 to 4 carbon atoms, respectively. Examples of the alkyl group are methyl group, ethyl group, n-propyl group, isopropyl group, n-butyl group, isobutyl group, sec-butyl group and tert-butyl group. $R^{10}$, $R^{11}$ and $R^{12}$ may be the same or different from each other. Among hydrogen atom and the groups described above, hydrogen atom, methyl group and ethyl group are preferable and it is preferred that at least one of $R^{10}$, $R^{11}$ and $R^{12}$ is hydrogen atom.

$R^{13}$ in the general formula (IX) is an alkylene group having 2 to 4 carbon atoms and, more specifically, ethylene group, trimethylene group, methylethylene group, tetramethylene group, 1,1-dimethylethylene group or 1,2-dimethylethylene group. Among them, alkylene groups having 2 or 3 carbon atoms are particularly preferable. In the general formula (IX), m is the number of repeating of $R^{13}O$, the average of which is in the range of 0 to 10 and preferably in the range of 0 to 5.

$R^{14}$ in the general formula (IX) is an alkyl group having 1 to 10 carbon atoms. Examples of the alkyl group are alkyl groups, such as methyl group, ethyl group, n-propyl group, isopropyl group, n-butyl group, isobutyl group, sec-butyl group, tert-butyl group, various kinds of pentyl group, various kinds of hexyl group, various kinds of heptyl groups, various kinds of octyl group and the like, cycloalkyl groups, such as cyclopentyl group, cyclohexyl group, various kinds of methylcyclohexyl group, various kinds of ethylcyclohexyl group, various kinds of dimethylcyclohexyl group and the like, and the like groups. Among them, alkyl groups having 8 or less carbon atoms are preferable. Alkyl groups having 1 to 6 carbon atoms are particularly preferable when m is 0 and alkyl groups having 1 to 4 carbon atoms are particularly preferable when m is 1 or more.

$R^{10}$ to $R^{14}$ may be the same or different between the constituting units and a plural of $R^{13}O$'s s may be the same or different from each other when the constituting unit contains a plural of $R^{13}O$'s.

It is necessary that the polyvinyl ether compound of the present invention does not contain any of an unsaturated bond, an acetal structure and an aldehyde structure in the molecule. The polyvinyl ether compound generally has the structure in which one end is expressed by the general formula (X):

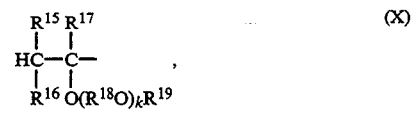

wherein $R^{15}$, $R^{16}$ and $R^{17}$ are a hydrogen atom or an alkyl group having 1 to 4 carbon atoms, respectively, and may be the same or different from each other, $R^{18}$ is an alkylene group having 2 to 4 carbon atoms, $R^{19}$ is an alkyl group having 1 to 10 carbon atoms, k is a number the average of which is in the range of 0 to 10 and a plural of $R^{18}O$'s may be the same or different from each other, and the other end is expressed by the general formula (XI):

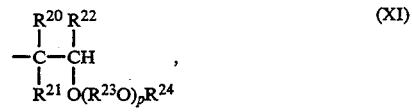

wherein $R^{20}$, $R^{21}$ and $R^{22}$ are a hydrogen atom or an alkyl group having 1 to 4 carbon atoms, respectively, and may be the same or different from each other, $R^{23}$ is an alkylene group having 2 to 4 carbon atoms, $R^{24}$ is an alkyl group having 1 to 10 carbon atoms, p is a number the average of which is in the range of 0 to 10 and a plural of $R^{23}O$'s may be the same or different from each other.

In the general formula (X) described above, $R^{15}$, $R^{16}$ and $R^{17}$ are a hydrogen atom or an alkyl group having 1 to 4 carbon atoms, respectively. Examples of the alkyl group are the same as those shown as examples in the description of $R^{10}$ to $R^{12}$ in the general formula (IX). $R^{15}$, $R^{16}$ and $R^{17}$ may be the same or different from each other. Among them, a hydrogen atom, methyl group and ethyl group are preferable and it is preferred that at least one of $R^{15}$, $R^{16}$ and $R^{17}$ is a hydrogen atom.

$R^{18}$ in the general formula (X) is an alkylene group having 2 to 4 carbon atoms. Examples of the alkylene group are the same as those shown as examples in the description of $R^{13}$ in the general formula (IX). Among them, alkylene groups having 2 or 3 carbon atoms are particularly preferable. In the general formula (X), k shows the repeating number of $R^{18}O$, the average of which is in the range of 0 to 10 and preferably in the range of 0 to 5. When a plural of $R^{18}O$'s are comprised, a plural of $R^{18}O$'s may be the same or different from each other.

$R^{19}$ in the general formula (X) is an alkyl group having 1 to 10 carbon atoms. Examples of the alkyl group are the same as those shown as examples in the description of $R^{14}$ in the general formula (IX). Among them, alkyl groups having 8 or less carbon atoms are preferable. Alkyl groups having 1 to 6 carbon atoms are particularly preferable when k is 0 and alkyl groups having 1 to 4 carbon atoms are particularly preferable when k is 1 or more.

In the general formula (XI) described above, $R^{20}$, $R^{21}$ and $R^{22}$ are a hydrogen atom or an alkyl group having 1 to 4 carbon atoms, respectively. Examples of the alkyl group are the same as those shown as examples in the description of $R^{10}$ to $R^{12}$ in the general formula (IX). $R^{20}$, $R^{21}$ and $R^{22}$ may be the same or different from each other. Among them, a hydrogen atom, methyl group and ethyl group are preferable and it is preferred that at least one of $R^{20}$, $R^{21}$ and $R^{22}$ is a hydrogen atom.

$R^{23}$ in the general formula (XI) is an alkylene group having 2 to 4 carbon atoms. Examples of the alkylene group are the same as those shown as examples in the description of $R^{13}$ in the general formula (IX). Among them, alkylene groups having 2 or 3 carbon atoms are particularly preferable. In the general formula (XI), p shows the repeating number of $R^{23}O$, the average of which is in the range of 0 to 10 and preferably in the range of 0 to 5. When a plural of $R^{23}O$'s are comprised, a plural of $R^{23}O$'s may be the same or different from each other.

$R^{24}$ in the general formula (XI) is an alkyl group having 1 to 10 carbon atoms. Examples of the alkyl group are the same as those shown as examples in the description of $R^{14}$ in the general formula (IX). Among them, alkyl groups having 8 or less carbon atoms are preferable. Alkyl groups having 1 to 6 carbon atoms are particularly preferable when p is 0 and alkyl groups having 1 to 4 carbon atoms are particularly preferable when p is 1 or more.

The polyvinyl ether compound of the present invention has the weight average molecular weight in the range of 300 to 3000, preferably the degree of polymerization in the range of 5 to 10 and the weight average molecular weight in the range of 400 to 2000 and more preferably the weight average molecular weight in the range of 400 to 1000. The ratio of the weight average molecular weight to the number average molecular weight is in the range of 1.05 to 2.00 and preferably in the range of 1.06 to 1.90.

The preferable compounds among the polyvinyl ether compounds of the present invention are compounds which have the constituting units expressed by the general formula (XII):

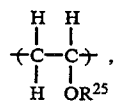

(XII)

wherein $R^{25}$ is an alkyl group having 1 to 4 carbon atoms and may be the same or different between the constituting units, do not contain any of an unsaturated bond, an acetal structure and an aldehyde structure and the weight average molecular weight in the range of 300 to 3000. The more preferable compounds among them are compounds which have the constituting units expressed by the general formula (XIII):

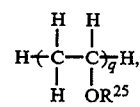

(VIII)

wherein $R^{25}$ is the same as described above and q is the degree of polymerization, and the weight average molecular weight in the range of 300 to 3000, more preferably in the range of 400 to 1000.

The polyvinyl ether compound of the present invention can be produced by (a) the process of polymerization of the corresponding vinyl ether monomer and (b) the process of treatment of unsaturated bonds and acetals in the polymerized product.

(a) Process of Polymerization

In the process of polymerization, the compound expressed by the general formula (XV):

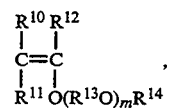

(XV)

wherein $R^{10}$ to $R^{14}$ and m are the same as those described above, is used as the vinyl ether monomer. As this vinyl ether monomer, various kinds of compound corresponding to the polyvinyl ether compounds described above are mentioned. Examples of such vinyl ether monomer are: vinyl methyl ether, vinyl ethyl ether, vinyl nopropyl ether, vinyl isopropyl ether, vinyl n-butyl ether, vinyl isobutyl ether, vinyl sec-butyl ether, vinyl tert-butyl ether, vinyl n-pentyl ether, vinyl n-hexyl ether, vinyl 2-methoxyethyl ether, vinyl 2-ethoxyethyl ether, vinyl 2-methoxy-1-methylethyl ether, vinyl 2-methoxypropyl ether, vinyl 3,6-dioxaheptyl ether, vinyl 3,6,9-trioxadecyl ether, vinyl 1,4-dimethyl-3,6-dioxaheptyl ether, vinyl 1,4,7-trimethyl-3,6,9-trioxadecyl ether, 1-methoxypropene, 1-ethoxypropene, 1-n-propoxypropene, 1-isopropoxypropene, 1-n-butoxypropene, 1-isobutoxypropene, 1-sec-butoxypropene, 1-tert-butoxypropene, 2-methoxypropene, 2-ethoxypropene, 2-n-propoxypropene, 2-isopropoxypropene, 2-n-butoxypropene, 2-isobutoxypropene, 2-sec-butoxypropene, 2-tert-butoxypropene, 1-methoxy-1-butene, 1-ethoxy-1-butene, 1-n-propoxy-1-butene, 1-isopropoxy-1-butene, 1-n-butoxy-1-butene, 1-isobutoxy-1-butene, 1-sec-butoxy-1-butene, 1-tert-butoxy-1-butene, 2-methoxy-1-butene, 2-ethoxy-1-butene, 2-n-propoxy-1-butene, 2-isopropoxy-1-butene, 2-n-butoxy-1-butene, 2-isobutoxy-1-butene, 2-sec-butoxy-1-butene, 2-tert-butoxy-1-butene, 2-methoxy-2-butene, 2-ethoxy-2-butene, 2-n-propoxy-2-butene, 2-isopropoxy-2-butene, 2-n-butoxy-2-butene, 2-isobutoxy-2-butene, 2-sec-butoxy-2-butene, 2-tert-butoxy-2-butene and the like. These vinyl ether monomers can be used singly or as a combination of two or more kinds. These vinyl ether monomers can be produced by conventional methods. As the method of polymerization of the vinyl ether monomers, radical polymerization, cationic polymerization or irradiation polymerization described in "Kobunshi Gosei III", edited by Shunsuke Murahashi, Minoru Imoto and Hisaya Tani (published by Asakura Shoten), can be adopted. A polymer having a desired viscosity can be obtained by the polymerization according to the method described in the following.

For initiating the polymerization, a combination of a Brønsted acid, a Lewis acid or an organometallic compound and water, an alcohol, a phenol, an acetal or an addition product of a vinyl ether and a carboxylic acid can be used as the initiator. Examples of the Brønsted acid are hydrofluoric acid, hydrochloric acid, hydrobromic acid, hydroiodic acid, nitric acid, sulfuric acid, trichloroacetic acid, trifluoroacetic acid and the like. Examples of the Lewis acid are boron trifluoride, aluminum trichloride, aluminum tribromide, tin tetrachloride, zinc dichloride, ferric chloride and the like. Among these Lewis acids, boron trifluoride and complexes thereof are particularly preferable. Examples of the organometallic compound are diethyl aluminum chloride, ethyl aluminum chloride, diethylzinc and the like.

As water, an alcohol, a phenol, an acetal or an addition product of a vinyl ether and a carboxylic acid used in combination with these compounds, a suitable compound can be selected and used according to desire.

Examples of the alcohol described above are: saturated aliphatic alcohols having 1 to 10 carbon atoms, such as methanol, ethanol, propanol, isopropanol, butanol, isobutanol, sec-butanol, tert-butanol, various kinds of pentanol, various kinds of hexanol, various kinds of heptanol, various kinds of octanol and the like; unsaturated aliphatic alcohols having 3 to 10 carbon atoms, such as allyl alcohol and the like; alcohols containing oxygen bonded as the ether bond, such as ethylene glycol monoalkyl ethers, ethylene glycol monoaryl ethers, propylene glycol monoalkyl ethers, propylene glycol monoaryl ethers, polyethylene glycol monoalkyl ethers, polyethylene glycol monoaryl ethers, polypropylene glycol monoalkyl ethers, polypropylene glycol monoaryl ethers and the like; and the like compounds. Among these compounds, aliphatic alcohols having 3 or less carbon atoms are preferable as the aliphatic alcohols and methanol and ethanol are particularly preferable. As the alcohol containing oxygen bonded as the ether bond, compounds of this structure having 14 or less carbon atoms are preferable.

Examples of the phenol are phenol, various kinds of cresol and the like compounds.

Examples of the acetal are acetaldehyde dimethyl acetal, acetaldehyde diethyl acetal, acetaldehyde methyl ethyl acetal, acetaldehyde di-n-propyl acetal, acetaldehyde methyl n-propyl acetal, acetaldehyde ethyl n-propyl acetal, acetaldehyde diisopropyl acetal, acetaldehyde methyl isopropyl acetal, acetaldehyde ethyl isopropyl acetal, acetaldehyde n-propyl isopropyl acetal, acetaldehyde di-n-butyl acetal, acetaldehyde methyl n-butyl acetal, acetaldehyde ethyl n-butyl acetal, acetaldehyde n-propyl n-butyl acetal, acetaldehyde isopropyl n-butyl acetal, acetaldehyde diisobutyl acetal, acetaldehyde methyl isobutyl acetal, acetaldehyde ethyl isobutyl acetal, acetaldehyde n-propyl isobutyl acetal, acetaldehyde isopropyl isobutyl acetal, acetaldehyde n-butyl isobutyl acetal, acetaldehyde di-sec-butyl acetal, acetaldehyde methyl sec-butyl acetal, acetaldehyde ethyl secobutyl acetal, acetaldehyde n-propyl sec-butyl acetal, acetaldehyde isopropyl sec-butyl acetal, acetaldehyde n-butyl sec-butyl acetal, acetaldehyde isobutyl sec-butyl acetal, acetaldehyde di-tert-butyl acetal, acetaldehyde methyl tert-butyl acetal, acetaldehyde ethyl tert-butyl acetal, acetaldehyde n-propyl tert-butyl acetal, acetaldehyde isopropyl tert-butyl acetal, acetaldehyde n-butyl tert-butyl acetal, acetaldehyde isobutyl tert-butyl acetal, acetaldehyde sec-butyl tert-butyl acetal, acetaldehyde di($\beta$-methoxyethyl) acetal, acetaldehyde di($\beta$-methoxyisopropyl) acetal, propionaldehyde dimethyl acetal, propionaldehyde diethyl acetal, propionaldehyde methyl ethyl acetal, propionaldehyde di-n-propyl acetal, propionaldehyde methyl n-propyl acetal, propionaldehyde ethyl n-propyl acetal, propionaldehyde diisopropyl acetal, propionaldehyde methyl isopropyl acetal, propionaldehyde ethyl isopropyl acetal, propionaldehyde n-propyl isopropyl acetal, propionaldehyde di-n-butyl acetal, propionaldehyde methyl n-butyl acetal, propionaldehyde ethyl n-butyl acetal, propionaldehyde n-propyl n-butyl acetal, propionaldehyde isopropyl n-butyl acetal, propionaldehyde diisobutyl acetal, propionaldehyde methyl isobutyl acetal, propionaldehyde ethyl isobutyl acetal, propionaldehyde n-propyl isobutyl acetal, propionaldehyde isopropyl isobutyl acetal, propionaldehyde n-butyl isobutyl acetal, propionaldehyde di-sec-butyl acetal, propionaldehyde methyl sec-butyl acetal, propionaldehyde ethyl sec-butyl acetal, propionaldehyde n-propyl sec-butyl acetal, propionaldehyde isopropyl sec-butyl acetal, propionaldehyde n-butyl sec-butyl acetal, propionaldehyde isobutyl sec-butyl acetal, propionaldehyde di-tert-butyl acetal, propionaldehyde methyl tert-butyl acetal, propionaldehyde ethyl tert-butyl acetal, propionaldehyde n-propyl tert-butyl acetal, propionaldehyde isopropyl tert-butyl acetal, propionaldehyde n-butyl tert-butyl acetal, propionaldehyde isobutyl tert-butyl acetal, propionaldehyde sec-butyl tert-butyl acetal, propionaldehyde di($\beta$-methoxyethyl) acetal, propionaldehyde di(b-methoxyisopropyl) acetal, n-butyraldehyde dimethyl acetal, n-butyraldehyde diethyl acetal, n-butyraldehyde methyl ethyl acetal, n-butyraldehyde di-n-propyl acetal, n-butyraldehyde methyl n-propyl acetal, n-butyraldehyde ethyl n-propyl acetal, n-butyraldehyde diisopropyl acetal, n-butyraldehyde methyl isopropyl acetal, n-butyraldehyde ethyl isopropyl acetal, n-butyraldehyde n-propyl isopropyl acetal, n-butyraldehyde di-n-butyl acetal, n-butyraldehyde methyl n-butyl acetal, n-butyraldehyde ethyl n-butyl acetal, n-butyraldehyde n-propyl n-butyl acetal, n-butyraldehyde isopropyl n-butyl acetal, n-butyraldehyde diisobutyl acetal, n-butyraldehyde methyl isobutyl acetal, n-butyraldehyde ethyl isobutyl acetal, n-butyraldehyde n-propyl isobutyl acetal, n-butyraldehyde isopropyl isobutyl acetal, n-butyraldehyde n-butyl isobutyl acetal, n-butyraldehyde di-sec-butyl acetal, n-butyraldehyde methyl sec-butyl acetal, n-butyraldehyde ethyl sec-butyl acetal, n-butyraldehyde n-propyl sec-butyl acetal, n-butyraldehyde isopropyl secobutyl acetal, n-butyraldehyde n-butyl sec-butyl acetal, n-butyraldehyde isobutyl sec-butyl acetal, n-butyraldehyde di-tert-butyl acetal, n-butyraldehyde methyl tert-butyl acetal, n-butyraldehyde ethyl tert-butyl acetal, n-butyraldehyde n-propyl tert-butyl acetal, n-butyraldehyde isopropyl tert-butyl acetal, n-butyraldehyde n-butyl tert-butyl acetal, n-butyraldehyde isobutyl tert-butyl acetal, n-butyraldehyde sec-butyl tert-butyl acetal, n-butyraldehyde di($\beta$-methoxyethyl) acetal, n-butyraldehyde di($\beta$-methoxyisopropyl) acetal and the like.

Examples of the carboxylic acid utilized for forming the addition product with a vinyl ether are acetic acid, propionic acid, n-butyric acid, isobutyric acid, n-valeric acid, isovaleric acid, 2-methylbutyric acid, pivalic acid, n-caproic acid, 2,2-dimehylbutyric acid, 2-methylvaleric acid, 3-methylvaleric acid, 4-methylvaleric acid, enanthic acid, 2-methylcaproic acid, caprylic acid, 2-ethylcaproic acid, 2-n-propylvaleric acid, n-nonanoic acid, 3,5,5-trimethylcaproic acid, undecanoic acid and the like. The vinyl ether may be the same as or different from those utilized for the polymerization and the specific examples are the same compounds as those mentioned as examples in the description of the vinyl ether monomers expressed by the general formula (XV). The addition product of the vinyl ether and the carboxylic acid can be obtained by mixing these compounds and conducting the reaction at a temperature around 0° to 100° C. The product may be utilized for the reaction after isolation with distillation or the like and may also be utilized for the reaction without isolation.

To the initiated end of the polymer, hydrogen is attached when water, an alcohol or a phenol is used and, when an acetal is used, the group formed by elimination of one of the alkoxy groups from the used acetal is attached. When an addition product of a vinyl ether to a carboxylic acid is used, the group formed by elimination of the alkylcarbonyloxy group derived from the carboxylic acid part from the addition product of the vinyl ether and the carboxylic acid is attached.

On the other hand, to the terminated end of the polymer, acetal, olefin or aldehyde is formed when water, an alcohol, a phenol or an acetal is used. When the addition product of a vinyl ether to a carboxylic acid is used, a carboxylic acid ester of hemiacetal is formed. When the carboxylic acid ester of hemiacetal is hydrolyzed in the presence of an acid, an aldehyde is formed.

Polymerization of the vinyl ether monomer expressed by the general formula (XV) is conducted at a temperature generally in the range of −80° to 150° C. and preferably 0° to 100° C. although the temperature is varied depending on the kinds of the materials and the catalyst or the initiator. The polymerization reaction is finished in a time of about 10 seconds to 10 hours.

For adjusting the molecular weight in the polymerization reaction, a polymer having lower average molecular weight can be obtained by increasing amount of an alcohol, water, a phenol, an acetal or the addition product of a vinyl ether and a carboxylic acid relative to the amount of the vinyl ether monomer expressed by the general formula (IX). A polymer having lower average molecular weight can be obtained also by increasing amount of the Bransted acid or the Lewis acid described above.

The polymerization can be performed without a solvent but a solvent may be used when the solvent is stable in the reaction condition. The kind of the solvent is not particularly limited. Preferable examples of the solvent are hydrocarbon solvents, such as hexane, benzene, toluene and the like, and ether solvents, such as ethyl ether, 1,2-dimethoxyethane, tetrahydrofuran and the like. The polymerization reaction can be terminated by adding an alkali.

(b) Process of Treatment

In this process, unsaturated bonds, acetals and aldehydes in the polymerized product are converted into saturated bonds and ethers.

(1) Unsaturated Bond

Unsaturated bonds formed at the end of the polymer by the polymerization can be converted into saturated bonds in conventional conditions, such as the reaction temperature of 20° to 200° C., the hydrogen pressure of 1 to 100 kg/cm$^2$ and in the presence of a hydrogenation catalyst. As the hydrogenation catalyst, platinum catalysts, palladium catalysts, rhodium catalysts, ruthenium catalysts, nickel catalysts, cobalt catalysts and the like are preferable.

The conversion can be performed also in the presence of the solid catalyst having acidic property and hydrogenation ability used in the method of production as the first object of the present invention described above.

(2) Acetal

The acetals can be efficiently converted to ethers by adopting the method of production of an ether compound as the first object of the present invention described above which is the method of hydrogenation in the presence of the solid catalyst having acidic property and hydrogenating ability. As the solid catalyst having acidic property and hydrogenating ability and conditions of the reaction adopted here, the solid catalyst and the conditions described in the method of production of an ether compound can be adopted. According to the method of the present invention, the ether compound can be produced from the acetal compound or the ketal compound with high conversion and high selectivity. In this process, because problem of corrosion does not arise, conventional apparatus of production can be used. Also, according to the method of the present invention, the acetal or the ketal is hydrogenized exclusively. Thus, even when the material acetal compound or the material ketal compound contains a hydrocarbon group containing ether oxygen, the part of ether oxygen is left unchanged and the acetal bond alone is converted to an ether bond.

The polyvinyl ether compound of the present invention is homopolymer or a copolymer of a vinyl ether monomer, contains none of unsaturated bonds, acetal structures and aldehyde structures in the molecule, has sufficiently excellent compatibility particularly with hydrogen-containing Flons, such as Flon 134a and the like, has excellent stability and lubricating property, has a volume specific resistance at 80° C. of $10^{12}$ $\Omega$.cm or more and is favorably used as a lubricating oil for compression-type refrigerators.

The polyvinyl ether compound is useful also as an electric insulating oil, an organic solvent, a surface active agent and the like.

The present invention is described with reference to examples in more detail in the following. However, the present invention is not limited by the examples.

The methods of measurements of the kinematic viscosity, the average molecular weights, the compatibility with Flon and the volume specific resistance and the method of hydrolysis testing of the polyvinyl ether compound are shown in the following.

(1) Kinematic Viscosity

Kinematic viscosity was measured according to the method of Japanese Industrial Standard K-2283 (1983) by using a glass capillary viscometer.

(2) Average Molecular Weights

Weight average molecular weight and number average molecular weight were measured by using the apparatus and in the conditions shown in the following and dispersion (weight average molecular weight/number average molecular weight) was obtained from these results.

Apparatus: a product of Nippon Bunko Kogyo Co., Ltd., 880-PU (pump). Shodex RI SE-61 (detector)

Column: TSK H8+G2000 H8+G1000 H8
Temperature: the room temperature
Solvent: THF (tetrahydrofuran)
Speed of elution: 1.4 ml/minute
Standard substance: polyethylene glycol (3) Compatibility Test A sample of a specified amount adjusted to make 5 weight % or 10 weight % based on Flon 134a (1,1,1,2-tetrafluoroethane) was charged into a pressure resistant glass ampoule and the ampoule was connected to the vacuum line and the line for Flon 134a gas. The ampoule was degassed in vacuum at the room temperature, cooled with liquid nitrogen and a specified amount of Flon 134a was taken into the ampoule. The ampoule was then sealed and the temperature at which the phase separation starts was measured by slowly cooling the sample from the room temperature to $-60°$ C. in a thermostatted vessel for the measurement of the compatibility at the lower temperature side and by slowly heating the sample from the room temperature to $+80°$ C. in a thermostatted vessel for the measurement of the compatibility at the higher temperature side. A lower temperature of the phase separation is preferable in the measurement at the lower temperature side and a higher temperature of the phase separation is preferable in the measurement at the higher temperature side.

(4) Volume Specific Resistance

A sample was dried under the reduced pressure (0.3 to 0.8 mmHg) at 100° C. for 1 hour and then charged into a liquid cell for the measurement of volume specific resistance which is placed into a thermostatted vessel at 80° C. After the sample was kept in the thermostatted vessel at 80° C. for 40 minutes, the volume specific resistance was measured at the added electric pressure of 250 V by using an ultrainsulation meter R8340 produced by Advantest Co.

(5) Hydrolysis Test

Into a bottle of pressure resistant glass of 250 ml capacity, 75 g of a sample, 25 g of water and a piece of copper (13×50 mm) were placed and the atmosphere in the bottle was replaced with nitrogen. The sample was kept in a rotatory thermostatted vessel at the temperature of 102° C. for 192 hours. After finishing the test, appearance of the sample and condition of the piece of copper were visually observed and the total acid value was measured.

Example of Catalyst Preparation 1

Into a flask, 100 g (containing water) of Raney nickel (a product of Kawaken Fine Chemical Co., Ltd., M300T) was charged and 100 g of absolute ethanol was added to it and mixed well. The mixture was left standing to have Raney nickel precipitated and the supernatant liquid was removed by decantation. The Raney nickel remaining in the flask was repeatedly treated with the treatment described above 5 times.

Example of Catalyst Preparation 2

Into a 100 ml flask of egg-plant type, 20 g of zeolite (a product of Toso Co., Ltd., HSZ330HUA) was charged. The flask was then dipped in an oil bath of 150° C. and evacuated by an oil rotary vacuum pump for 1 hour. After cooling to the room temperature, the flask was brought to the atmospheric pressure by introducing dry nitrogen.

Example of Catalyst Preparation 3

Into a 100 ml flask of egg-plant type, 20 g of activated clay (a product of Wako Jun-yaku Co., Ltd.) was charged. The flask was then dipped in an oil bath of 150° C. and evacuated by an oil rotary vacuum pump for 1 hour. After cooling to the room temperature, the flask was brought to the atmospheric pressure by introducing dry nitrogen.

Example 1

Into a 1 liter autoclave made of SUS-316L, 100 g of acetaldehyde diethyl acetal, 100 g of n-heptane, 3.0 g of Raney nickel prepared in Example of Catalyst Preparation 1 (in the condition wet with ethanol) and 3.0 g of zeolite prepared in Example of Catalyst Preparation 2 were charged. Hydrogen was introduced into the autoclave and the pressure of hydrogen was adjusted to 10 kg/cm$^2$. After stirring for about 30 seconds, the pressure was released. Hydrogen was introduced into the autoclave again to make the pressure of hydrogen 10 kg/cm$^2$ and, after stirring for about 30 seconds, the pressure of hydrogen was released. Then, the pressure of hydrogen was increased to 30 kg/cm$^2$ and the temperature was increased to 130° C. in 30 minutes under stirring. The reaction was conducted at 130° C. for 2 hours and 30 minutes. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 30 kg/cm$^2$ during the reaction. After finishing the reaction, the reaction mixture was cooled to 20° C. and the pressure was decreased to the atmospheric pressure. Qualitative analysis and quantitative analysis were made with the reaction solution by the gas chromatography. The conversion of acetaldehyde diethyl acetal was 94.9% and the selectivity of diethyl ether was 68.3%.

Example 2

Into a 1 liter autoclave made of SUS-316L, 100 g of propionaldehyde diethyl acetal, 100 g of n-octane, 6.0 g of Raney nickel prepared in Example of Catalyst Preparation 1 (in the condition wet with ethanol) and 6.0 g of zeolite prepared in Example of Catalyst Preparation 2 were charged. Hydrogen was introduced into the autoclave and the pressure of hydrogen was adjusted to 10 kg/cm$^2$. After stirring for about 30 seconds, the pressure was released. Hydrogen was introduced into the autoclave again to make the pressure of hydrogen 10 kg/cm$^2$ and, after stirring for about 30 seconds, the pressure of hydrogen was released. Then, the pressure of hydrogen was increased to 30 kg/cm$^2$ and the temperature was increased to 130° C. in 30 minutes under stirring. The reaction was conducted at 130° C. for 1 hour and 30 minutes. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 30 kg/cm$^2$ during the reaction. After finishing the reaction, the reaction mixture was cooled to 20° C. and the pressure was decreased to the atmospheric pressure. Qualitative analysis and quantitative analysis were conducted with the reaction product by the gas chromatography. The conversion of propionaldehyde diethyl acetal was 97.0% and the selectivity of ethyl n-propyl ether was 72.0%.

Example 3

(1) Preparation of Material

Into a 5 liter glass flask equipped with a dropping funnel, a cooler and a stirrer, 1000 g of toluene, 500 g of acetaldehyde diethyl acetal and 5.0 g of boron trifluoride diethyl etherate were charged. Into a dropping funnel, 2500 g of ethyl vinyl ether was charged and dropped in 2 hours and 30 minutes. During this period, the reaction started and the temperature of the reaction solution increased. The temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 2833 g of the product. The $^1$H-NMR chart of this product is shown in FIG. 1. From this figure, the product was found to have the structures of the following formulae (A) and (B). The product had the kinematic viscosity of 5.18 cSt at 100° C. and 38.12 cSt at 40° C.

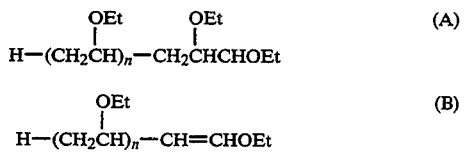

The ratio of numbers of molecule was (A):(B)=4.5:1 and the average value of n was 5.6.

(2) Into a 1 liter autoclave made of SUS-316L, 200 g of the oligomer prepared in (1) described above, 6.0 g of Raney nickel prepared in Example of Catalyst Preparation 1 (in the condition wet with ethanol) and 6.0 g of zeolite prepared in Example of Catalyst Preparation 2 were charged. Hydrogen was introduced into the autoclave and the pressure of hydrogen was adjusted to 10 kg/cm$^2$. After stirring for about 30 seconds, the pressure was released. Hydrogen was introduced into the autoclave again to make the pressure of hydrogen 10 kg/cm$^2$ and, after stirring for about 30 seconds, the pressure of hydrogen was released. After repeating this operation once more, the pressure of hydrogen was increased to 25 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 25 kg/cm$^2$ during the reaction. After finishing the reaction, the reaction mixture was cooled to the room temperature and the pressure was decreased to the atmospheric pressure. To the reaction mixture, 100 ml of hexane was added. The catalyst was precipitated by standing for 30 minutes and the reaction solution was removed by decantation. The hexane solution was combined with the reaction solution and filtered with filter paper. The catalyst was recycled in Example 5. Hexane, water and the like were removed under the reduced pressure by using a rotary evaporator. The yield was 162 g.

Figure 2:
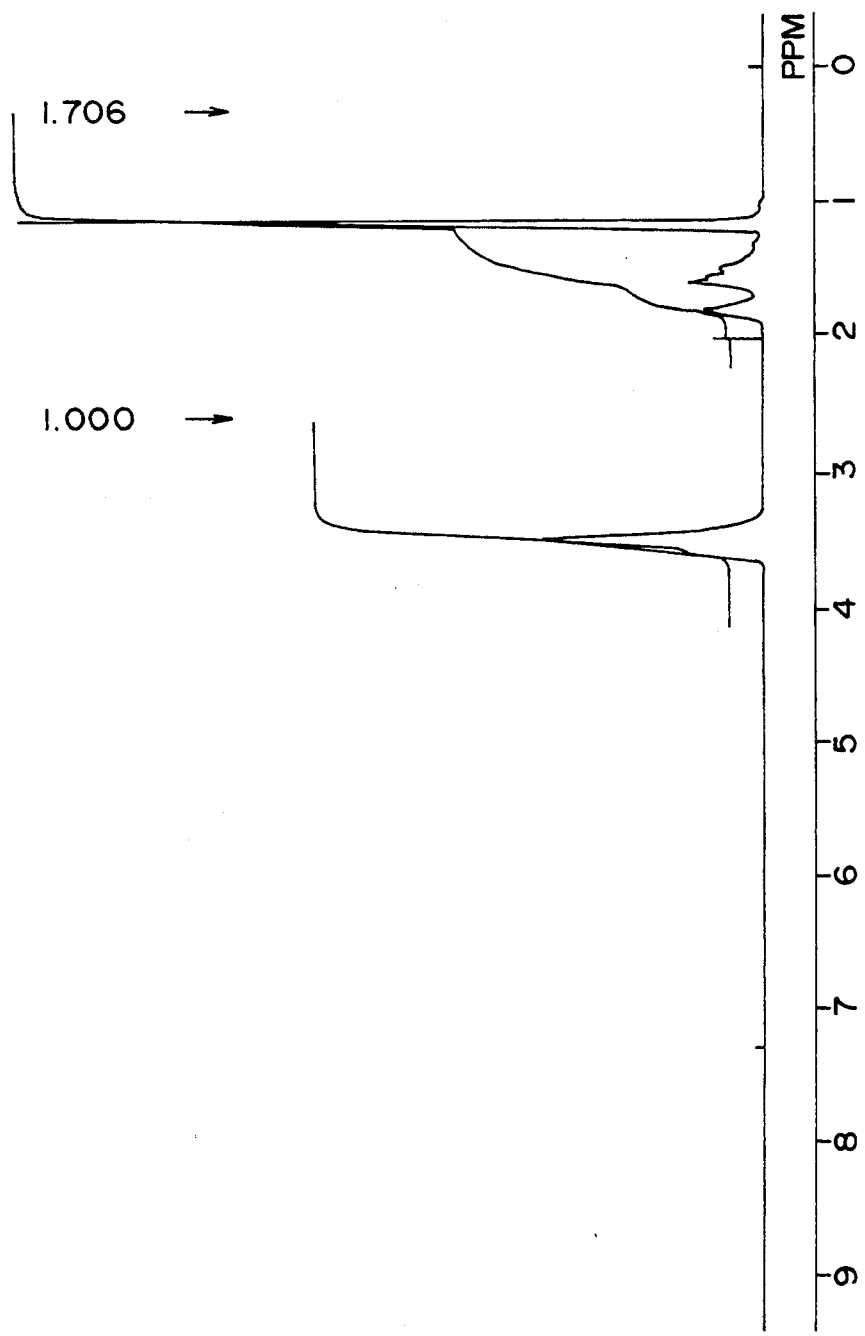

The $^1$H-NMR chart of this product is shown in FIG. 2. From this chart, the material acetal was found to have been converted to the ether compound shown by the formula (C):

wherein Et is an ethyl group. The conversion was 100%. The kinematic viscosity was 4.90 at 100° C. and 29.50 at 40° C. The oligomer of ethyl vinyl ether having the formula (B) described above was also converted to the ether compound having the formula (C) described above.

Example 4

Into a 1 liter autoclave made of SUS-316L, 200 g of the oligomer prepared in Example 3 (1) described above, 20 g of Raney nickel prepared in Example of Catalyst Preparation 1 (in the condition wet with ethanol) and 20 g of zeolite prepared in Example of Catalyst Preparation 2 were charged. Hydrogen was introduced into the autoclave and the pressure of hydrogen was adjusted to 7 kg/cm$^2$. After stirring for about 30 seconds, the pressure was released. After repeating this operation once more, the pressure of hydrogen was brought to 7 kg/cm$^2$ and the temperature was increased to 130° C. in 30 minutes under stirring. The reaction was conducted at 130° C. for 2 hours and 30 minutes. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 7 kg/cm$^2$ during the reaction. After finishing the reaction, the reaction mixture was cooled to the room temperature and the pressure was decreased to the atmospheric pressure. The reaction mixture was filtered and water and the like were removed from the solution part under the reduced pressure by using a rotary evaporator. The yield was 160 g. By this procedure, the same ether compound as that in Example 3 (2) was obtained from the material acetal and the conversion was 100%. The kinematic viscosity was 4.77 at 100° C. and 30.27 at 40° C.

Example 5

In the autoclave used in Example 3 (2) in which the catalyst was remaining, 200 g of the oligomer prepared in Example 3 (1) was charged and the reaction was performed by the same method as in Example 3 (2). The yield was 164 g. By this procedure, the same ether compound was obtained as that in Example 3 (2) from the material acetal and the conversion was 100%. The kinematic viscosity was 4.93 at 100° C. and 29.13 at 40° C.

Example 6

(1) Preparation of Material

The reaction was performed by the same method as in Example 3 (1) except that the amount of acetaldehyde diethyl acetal was 450 g, the amount of boron trifluoride etherate was 4.5 g and the amount of ethyl vinyl ether was 2800 g. The yield was 3175 g. The product had the same structure as that in Example 3 (1). The kinematic viscosity was 6.79 at 100° C. and 59.68 at 40° C. The ratio of the numbers of molecule was (A): (B)=8:1 and the average value of n was 6.8.

(2) Into a 1 liter autoclave made of SUS-316L, 200 g of the oligomer prepared in (1) described above, 10 g of Raney nickel prepared in Example of Catalyst Preparation 1 (in the condition wet with ethanol) and 15 g of activated clay prepared in Example of Catalyst Preparation 3 were charged. Hydrogen was introduced into the autoclave and the pressure of hydrogen was adjusted to 10 kg/cm². After stirring for about 30 seconds, the pressure was released. Hydrogen was introduced into the autoclave again and the pressure of hydrogen was adjusted to 10 kg/cm². After stirring for about 30 seconds, the pressure was released. After repeating this operation once more, the pressure of hydrogen was increased to 30 kg/cm² and the temperature was increased to 150° C. in 40 minutes under stirring. The reaction was conducted at 150° C. for 1 hour. The reaction proceeded during and after the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 30 kg/cm² during the reaction. After finishing the reaction, the reaction mixture was cooled to the room temperature and the pressure was decreased to the atmospheric pressure. The reaction mixture was filtered and water and the like were removed from the solution part under the reduced pressure by using a rotary evaporator. The yield was 158 g. By this procedure, the same ether compound as in Example 3 (2) was obtained from the material acetal and the conversion was 100%. The kinematic viscosity was 7.06 at 100° C. and 57.32 at 40° C.

Example 7

Into a 1 liter autoclave made of SUS-316L, 200 g of the oligomer prepared in Example 3 (1) described above, 10 g of zeolite prepared in Example of Catalyst Preparation 2 and 5.0 g of Pd/C (supporting 5% of Pd, a product of Wako Jun-yaku Co., Ltd.) were charged. Hydrogen was introduced into the autoclave and the pressure of hydrogen was adjusted to 7 kg/cm². After stirring for about 30 seconds, the pressure was released. Hydrogen was introduced into the autoclave again and the pressure of hydrogen was adjusted to 7 kg/cm². After stirring for about 30 seconds, the pressure was released. After repeating this operation once more, the pressure of hydrogen was brought to 7 kg/cm² and the temperature was increased to 120° C. in 30 minutes under stirring. The reaction was conducted at 120° C. for 7 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 7 kg/cm² during the reaction. After finishing the reaction, the reaction mixture was cooled to the room temperature and the pressure was decreased to the atmospheric pressure. The reaction mixture was filtered and water and the like were removed from the solution part under the reduced pressure by using a rotary evaporator. The yield was 167.2 g. By this procedure, the same ether compound as in Example 3 (2) was obtained from the material acetal and the conversion was 100%. The kinematic viscosity was 5.28 at 100° C. and 32.93 at 40° C.

Example 8

Into a 1 liter autoclave made of SUS-316L, 200 g of the oligomer prepared in Example 3 (1) described above, 20 g of zeolite prepared in Example of Catalyst Preparation 2 and 20 g of Ru/C (supporting 5% of Ru, a product of Wako Jun-yaku Co., Ltd.) were charged. Hydrogen was introduced into the autoclave and the pressure of hydrogen was adjusted to 30 kg/cm². After stirring for about 30 seconds, the pressure was released. Hydrogen was introduced into the autoclave again and the pressure of hydrogen was adjusted to 30 kg/cm². After stirring for about 30 seconds, the pressure was released. After repeating this operation once more, the pressure of hydrogen was brought to 30 kg/cm² and the temperature was increased to 130° C. in 30 minutes under stirring. The reaction was conducted at 130° C. for 1 hour. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 30 kg/cm² during the reaction. After finishing the reaction, the reaction mixture was cooled to the room temperature and the pressure was decreased to the atmospheric pressure. The reaction mixture was filtered and water and the like were removed from the solution part under the reduced pressure by using a rotary evaporator. The yield was 156 g. By this procedure, the same ether compound as in Example 3 (2) was obtained from the material acetal and the conversion was 100%. The kinematic viscosity was 5.18 at 100° C. and 31.53 at 40° C.

Example 9

Into a 1 liter autoclave made of SUS-316L, 15 g of Ni-diatomaceous earth and 350 g of hexane were charged. After replacing the atmosphere in the autoclave with hydrogen, the pressure of hydrogen was adjusted to 30 kg/cm². The temperature was increased to 150° C. in 30 minutes under stirring and the activation treatment of the catalyst was conducted for 30 minutes. After cooling the autoclave, 300 g of the oligomer prepared in Example 3 (1) and 15 g of zeolite prepared in Example of Catalyst Preparation 2 were charged into the autoclave. Hydrogen was introduced into the autoclave and the pressure of hydrogen was adjusted to 30 kg/cm². After stirring for about 30 seconds, the pressure was released. Hydrogen was introduced into the autoclave again and the pressure of hydrogen was adjusted to 30 kg/cm². After stirring for about 30 seconds, the pressure was released. After repeating this operation once more, the pressure of hydrogen was brought to 30 kg/cm² and the temperature was increased to 130° C. in 30 minutes under stirring. The reaction was conducted at 130° C. for 1 hour. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 30 kg/cm² during the reaction. After finishing the reaction, the reaction mixture was cooled to the room temperature and the pressure was decreased to the atmospheric pressure. The reaction mixture was filtered and hexane, water and the like were removed from the solution part under the reduced pressure by using a rotary evaporator. The yield was 240 g.

The conversion of the material acetal was 100% like in Example 3. The kinematic viscosity was 5.38 at 100° C. and 33.12 at 40° C.

Example 10

(1) Preparation of Polymer of Ethyl Vinyl Ether

Into a 5 liter glass flask equipped with a dropping funnel, a cooler and a stirrer, 1000 g of toluene, 304 g of ethanol and 7.8 g of boron trifluoride diethyl etherate were charged. Into a dropping funnel, 3284 g of ethyl vinyl ether was charged and dropped in 4 hours and 30 minutes. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 1100 ml of a 5 weight % aqueous solution of sodium hydroxide 3 times and then with 1100 ml of water 3 times. The solvent and unreacted materials were removed under the reduced pressure by using a rotary evaporator to obtain 3397 g of the crude product. The crude product had the kinematic viscosity of 17.8 cSt at 40° C.

$^1$H-NMR and $^{13}$C-NMR of the crude product were measured. The $^1$H-NMR showed peaks at 4.7 ppm, 5.35 ppm and 5.6 ppm and the $^{13}$C-NMR showed peaks at 101 ppm, 129 ppm and 134 ppm.

Into a 2 liter autoclave made of SUS-316L, 600 g of the crude product, 600 g of hexane, 18 g of Raney nickel prepared in Example of Catalyst Preparation 1 and 18 g of zeolite prepared in Example of Catalyst Preparation 2 were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was removed by decantation. The catalyst was washed with 100 ml of hexane twice. The washing liquid was combined with the reaction liquid and filtered with filter paper. The combined liquid was then transferred to a washing vessel and washed with 500 ml of a 5 weight % aqueous solution of sodium hydroxide 3 times and then with 500 ml of distilled water 5 times. Hexane, water and the like were removed under the reduced pressure by using a rotary evaporator. The yield was 492 g.

(2) Evaluation

Kinematic viscosity, average molecular weights and dispersion of molecular weight, compatibility with Flon, volume specific resistance and resistance to hydrolysis of the ethyl vinyl ether polymer obtained in (1) described above were measured. The results of the measurements are shown in Table 1.

Figure 3:
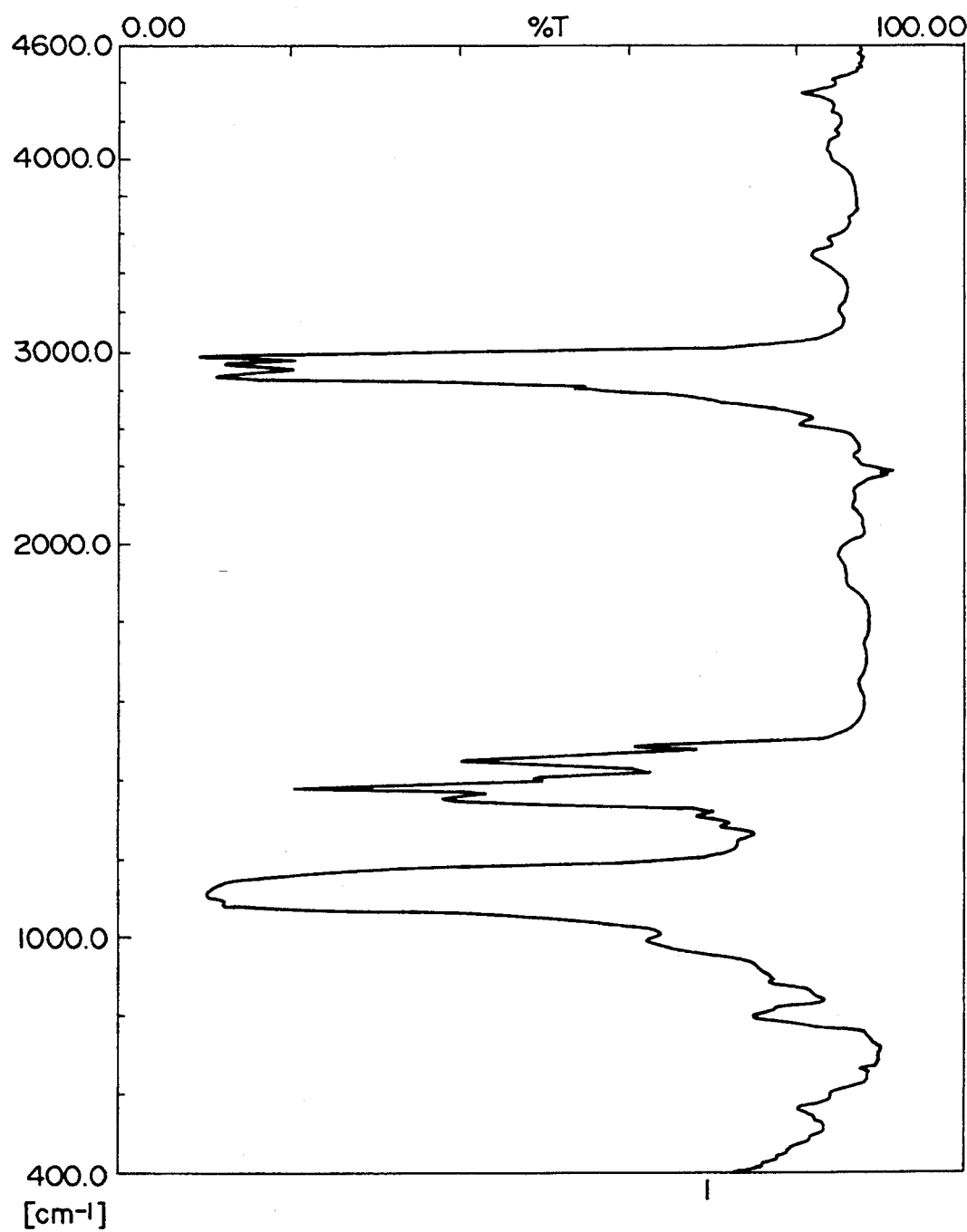
FIG. 3, FIG. 6, FIG. 9, FIG. 12, FIG. 15, FIG. 16, FIG. 19, FIG. 22, FIG. 25 and FIG. 28 are the infrared absorption spectra of the polyvinyl ether compounds obtained in Examples 10, 11, 12, 13, 14, 15, 16, 17, 18 and 19, respectively.
Figure 4:
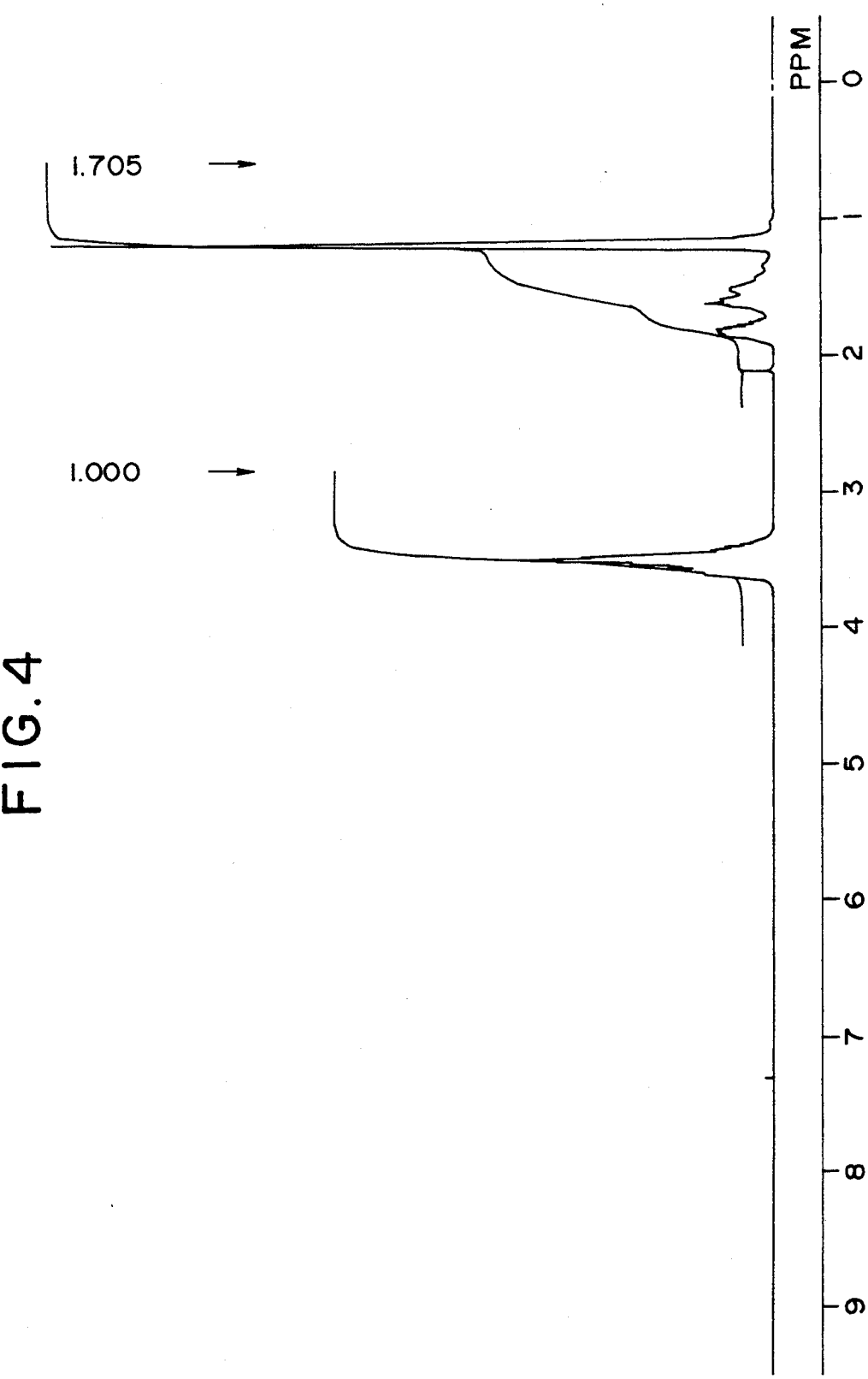
FIG. 4, FIG. 7, FIG. 10, FIG. 13, FIG. 17, FIG. 20, FIG. 23, FIG. 26 and FIG. 29 are the $^1$H-NMR charts of the polyvinyl ether compounds obtained in Examples 10, 11, 12, 13, 15, 16, 17, 18 and 19, respectively.
Figure 5:
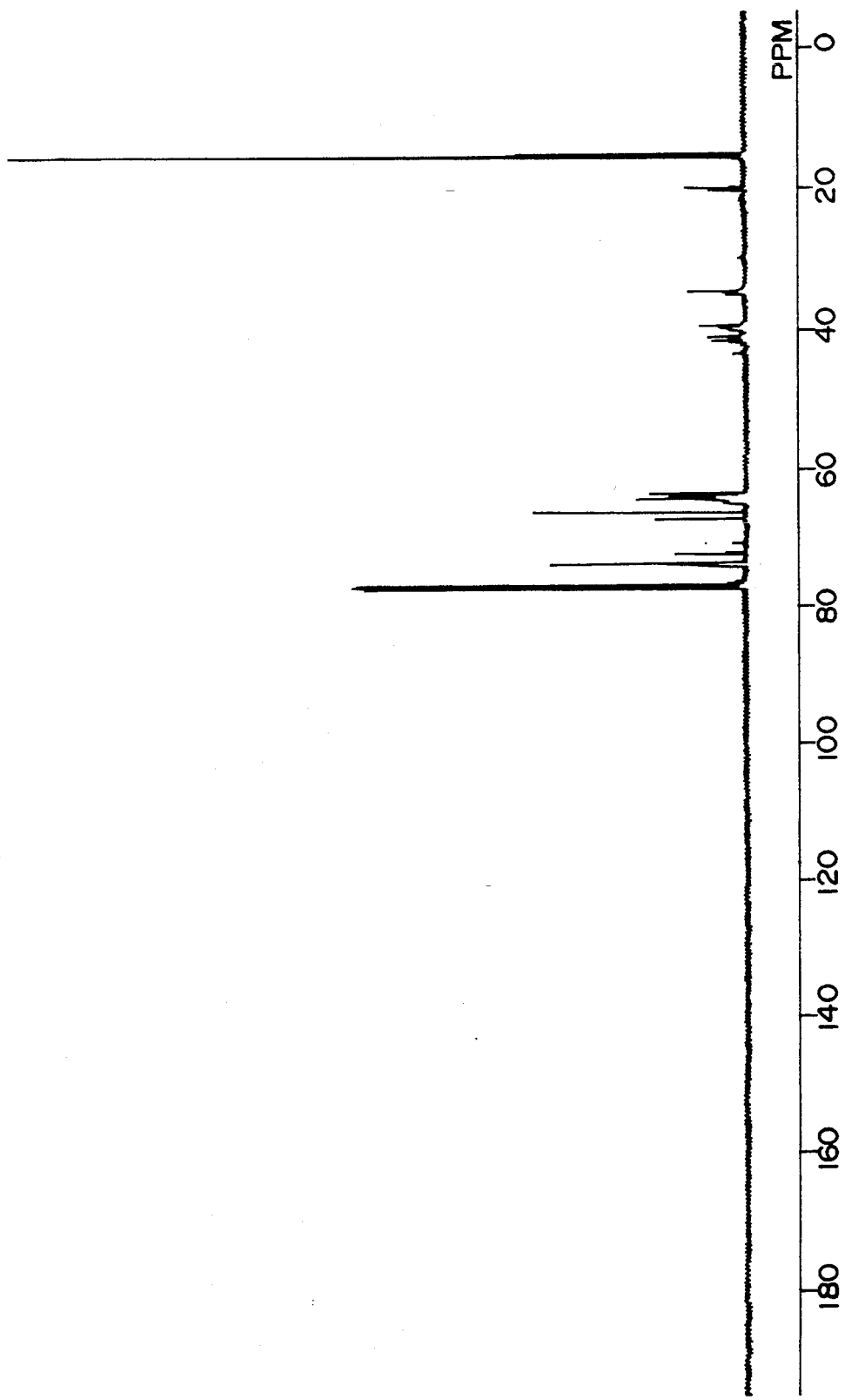
FIG. 5, FIG. 8, FIG. 11, FIG. 14, FIG. 18, FIG. 21, FIG. 24, FIG. 27 and FIG. 30 are the $^{13}$C-NMR charts of the polyvinyl ether compounds obtained in Examples 10, 11, 12, 13, 15, 16, 17, 18 and 19, respectively.

The infrared absorption spectrum is shown in FIG. 3, the $^1$H-NMR chart is shown in FIG. 4 and the $^{13}$C-NMR chart is shown in FIG. 5.

In the $^1$H-NMR chart of this polymer, the peaks at 4.7 ppm, 5.35 ppm and 5.6 ppm observed in the chart of the crude product described above were not found. In the $^{13}$C-NMR chart of this polymer, the peaks at 101 ppm, 129 ppm and 134 ppm were not found either. Furthermore, although the $^1$H-NMR peak derived from the hydrogen of aldehyde is generally found in the area of 9.7 ppm and the $^{13}$C-NMR peak derived from the carbon of aldehyde is generally found in the area of 200 ppm, none of these peaks were found in the spectra of the polymer obtained above.

From these findings, it can be found that the polymer obtained above did not contain any of an unsaturated bond, an acetal structure and an aldehyde structure.

Example 11

(1) Preparation of Polymer of Ethyl Vinyl Ether

Into a 5 liter glass flask equipped with a dropping funnel, a cooler and a stirrer, 1000 g of toluene, 500 g of acetaldehyde diethyl acetal and 5.0 g of boron trifluoride diethyl etherate were charged. Into a dropping funnel, 2700 g of ethyl vinyl ether was charged and dropped in 3 hours. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 3040 g of the crude product. The crude product had the kinematic viscosity of 42.1 cSt at 40° C. Into a 2 liter autoclave made of SUS-316L, 600 g of the crude product, 600 g of hexane, 18 g of Raney nickel prepared in Example of Catalyst Preparation 1 and 18 g of zeolite prepared in Example of Catalyst Preparation 2 were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm² during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a washing vessel and washed with 500 ml of a 5 weight % aqueous solution of sodium hydroxide 3 times and then with 500 ml of distilled water 5 times. Hexane, water and the like were removed under the reduced pressure by using a rotary evaporator. The yield was 495 g.

(2) Evaluation

Kinematic viscosity, average molecular weights and dispersion of molecular weight, compatibility with Flon, volume specific resistance and resistance to hydrolysis of the ethyl vinyl ether polymer obtained in (1) described above were measured. The results of the measurements are shown in Table 1.

Figure 6:
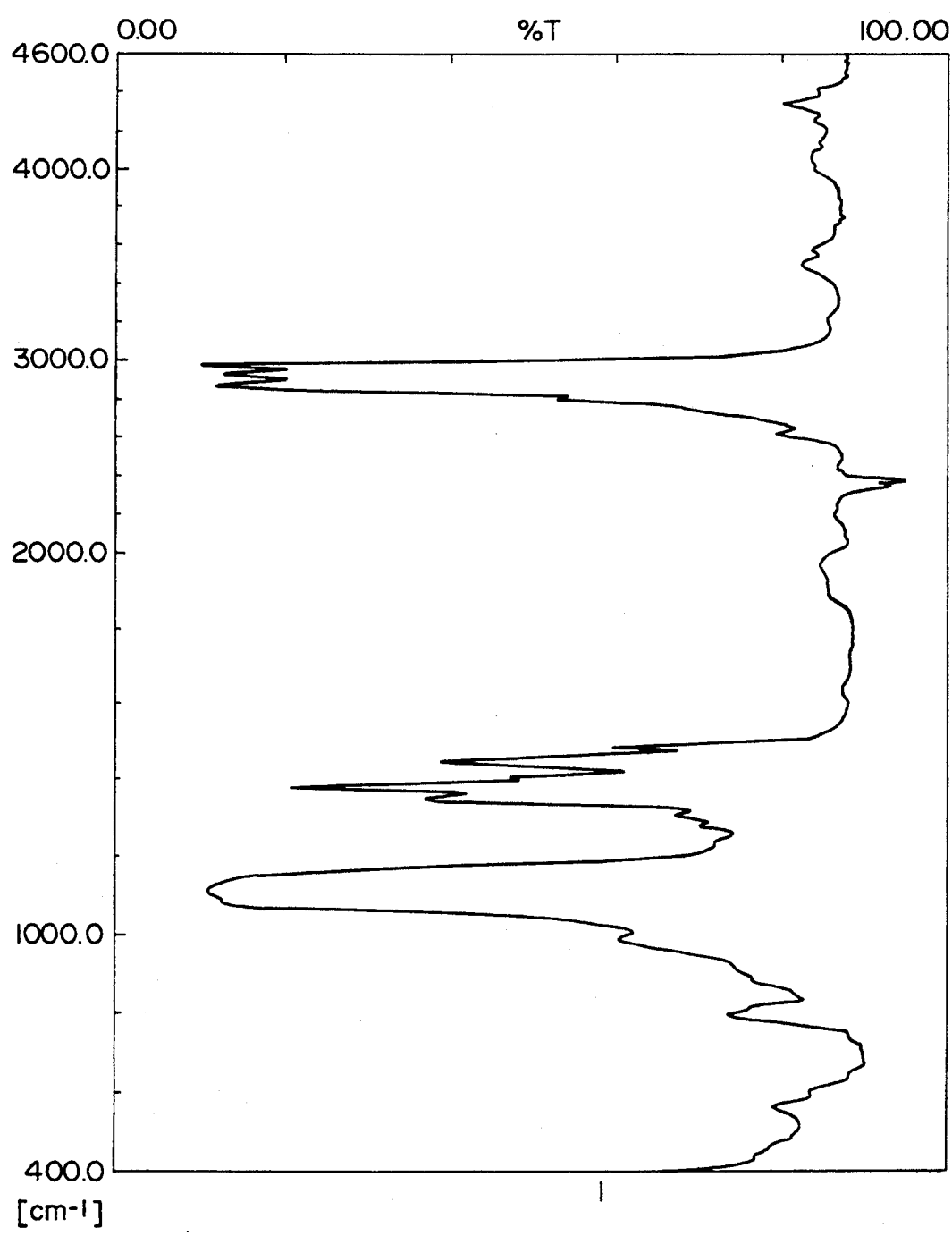
Figure 7:
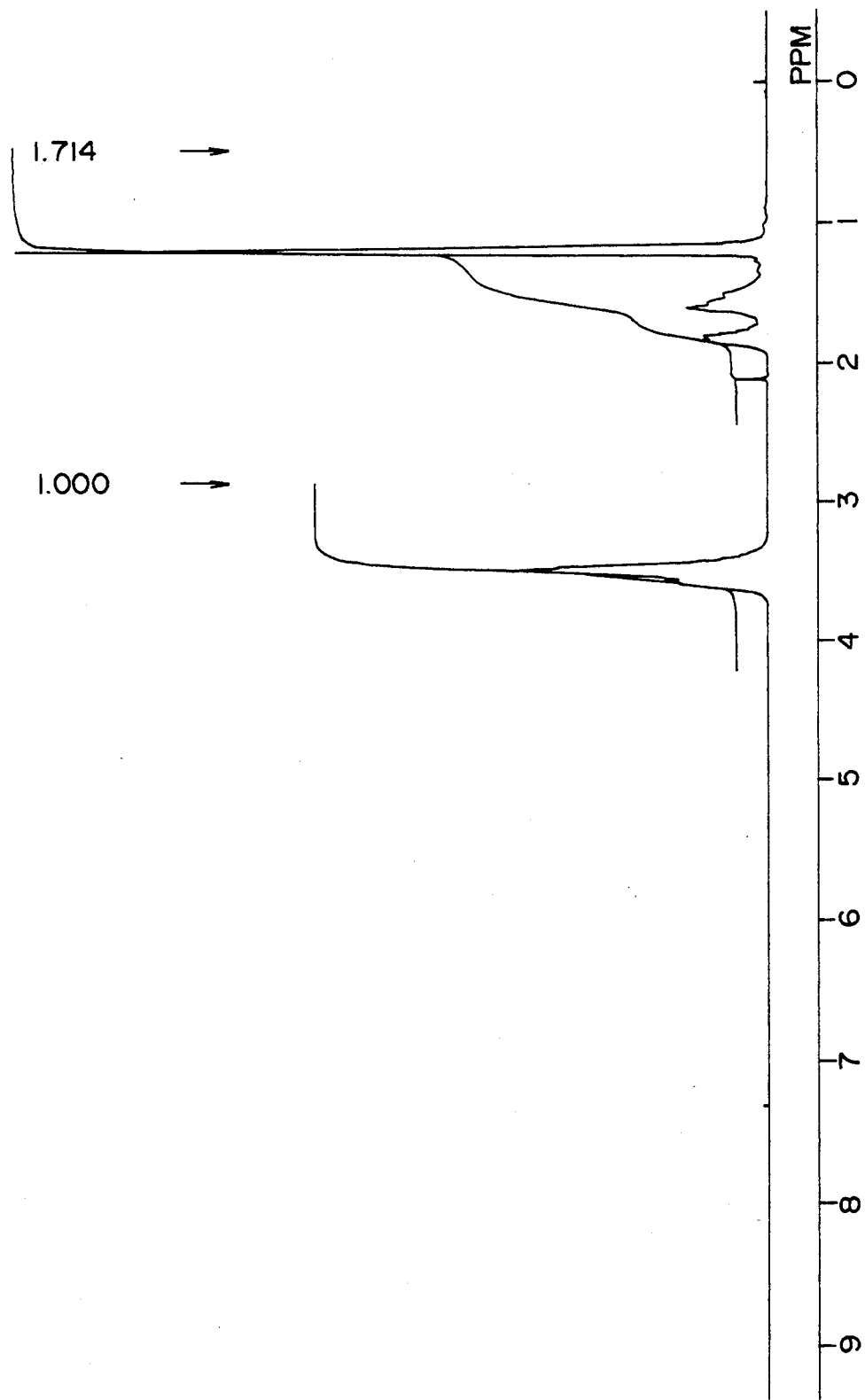
Figure 8:
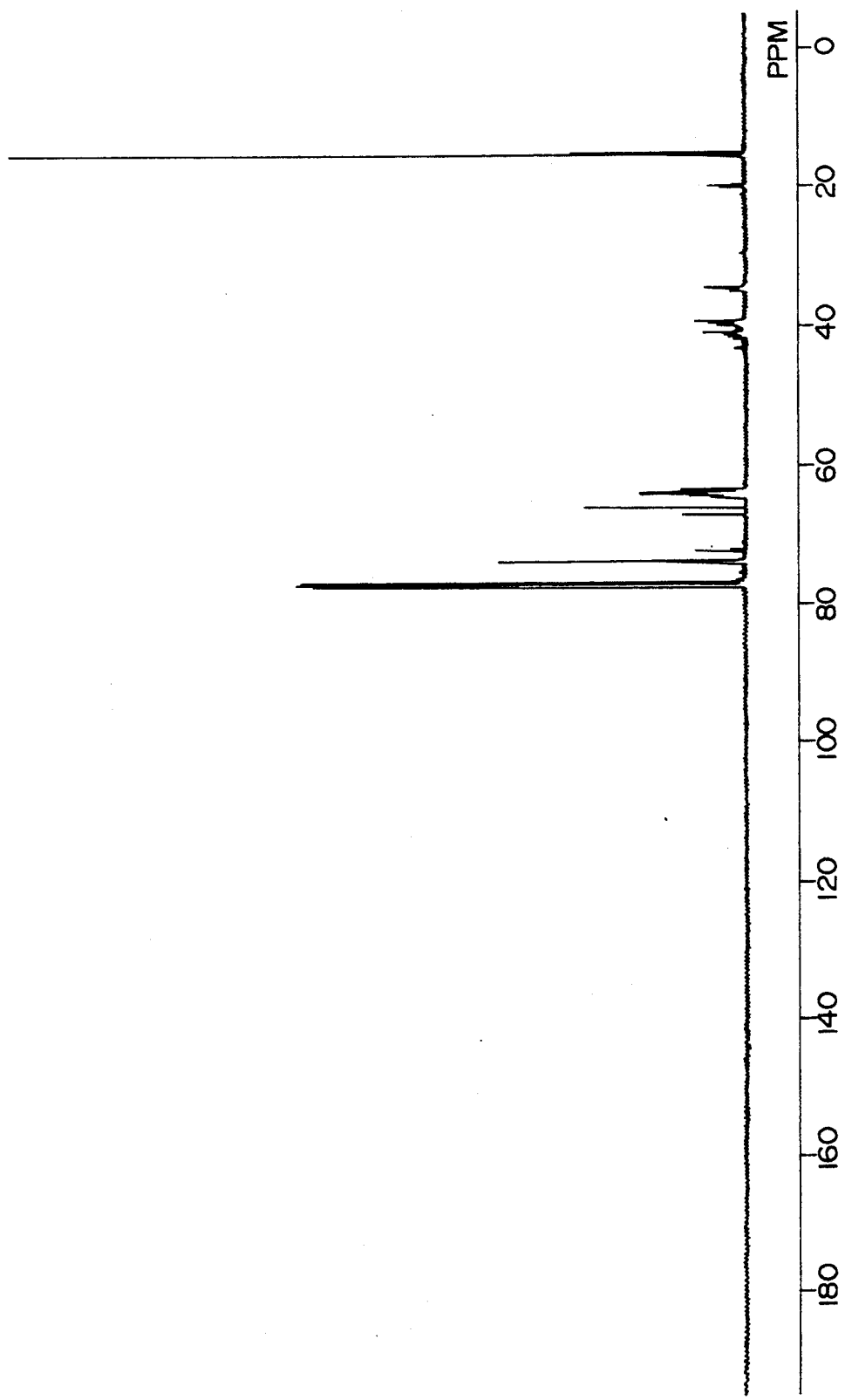

The infrared absorption spectrum is shown in FIG. 6, the $^1$H-NMR chart is shown in FIG. 7 and the $^{13}$C-NMR chart is shown in FIG. 8.

By the same reason as that described in Example 10, the polymer obtained above did not contain any of an unsaturated bond, an acetal structure and an aldehyde structure.

Example 12

(1) Preparation of Polymer of Ethyl Vinyl Ether

Into a 5 liter glass flask equipped with a dropping funnel, a cooler and a stirrer, 1000 g of toluene, 450 g of acetaldehyde diethyl acetal and 4.5 g of boron trifluoride diethyl etherate were charged. Into a dropping funnel, 3200 g of ethyl vinyl ether was charged and dropped in 4 hours and 10 minutes. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 3466 g of the crude product. The crude product had the kinematic viscosity of 76.1 cSt at 40° C.

Into a 2 liter autoclave made of SUS-316L, 600 g of the crude product, 600 g of hexane, 18 g of Raney nickel prepared in Example of Catalyst Preparation 1 and 18 g of zeolite prepared in Example of Catalyst Preparation 2 were charged. Hydrogen was introduced into the autoclave and the pressure of hydrogen was adjusted to 20 kg/cm². After stirring for about 30 seconds, the pressure was released. Hydrogen was introduced into the autoclave again to make the pressure of hydrogen 20 kg/cm² and, after stirring for about 30 seconds, the pressure of hydrogen was released. After repeating this operation once more, the pressure of hydrogen was increased to 50 kg/cm² and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm² during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a washing vessel and washed with 500 ml of a 5 weight % aqueous solution of sodium hydroxide 3 times and then with 500 ml of distilled water 5 times. Hexane, water and the like were removed under the reduced pressure by using a rotary evaporator. The yield was 498 g.

(2) Evaluation

Kinematic viscosity, average molecular weights and dispersion of molecular weight, compatibility with Flon, volume specific resistance and resistance to hydrolysis of the ethyl vinyl ether polymer obtained in (1) described above were measured. The results of the measurements are shown in Table 1.

Figure 9:
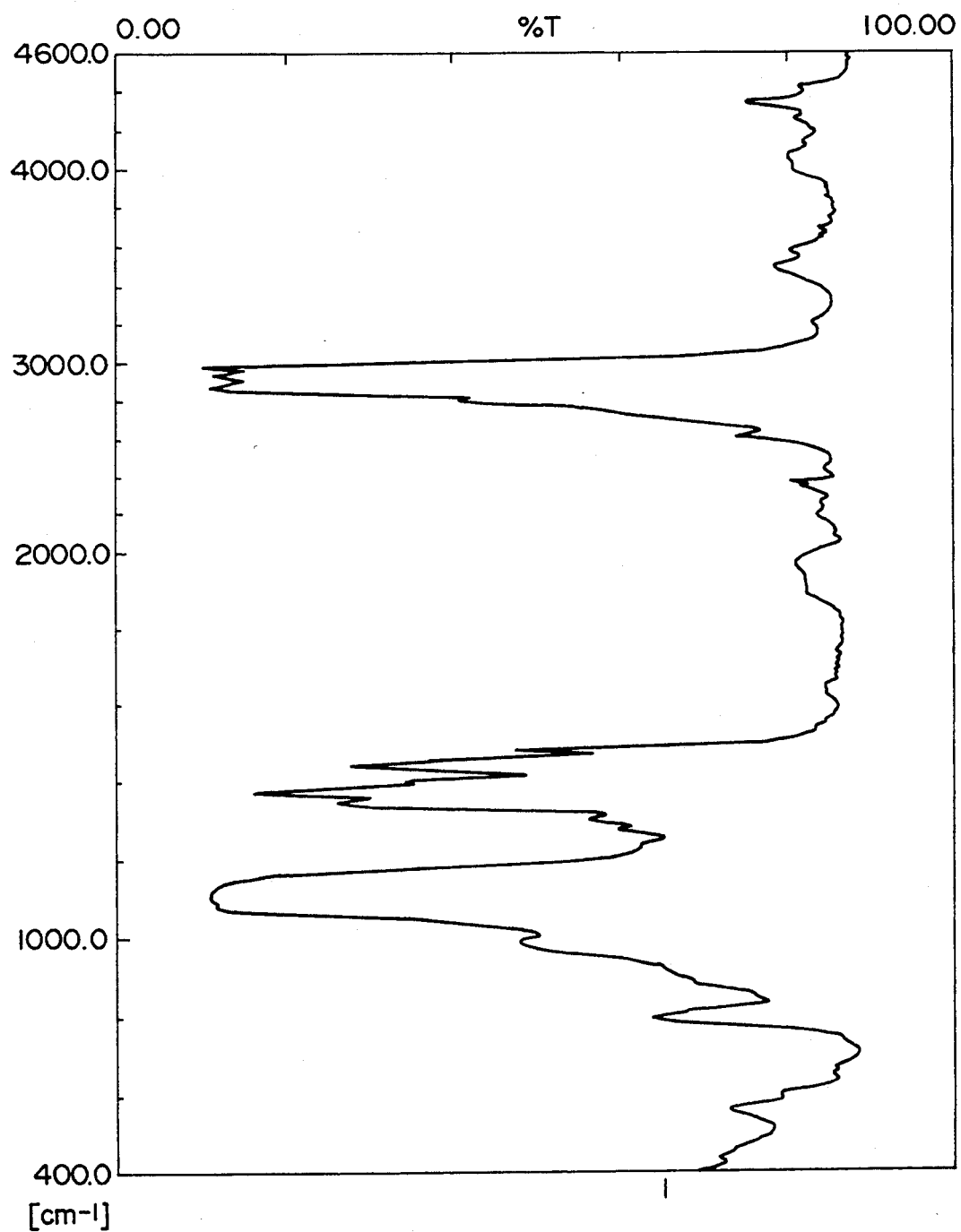
Figure 10:
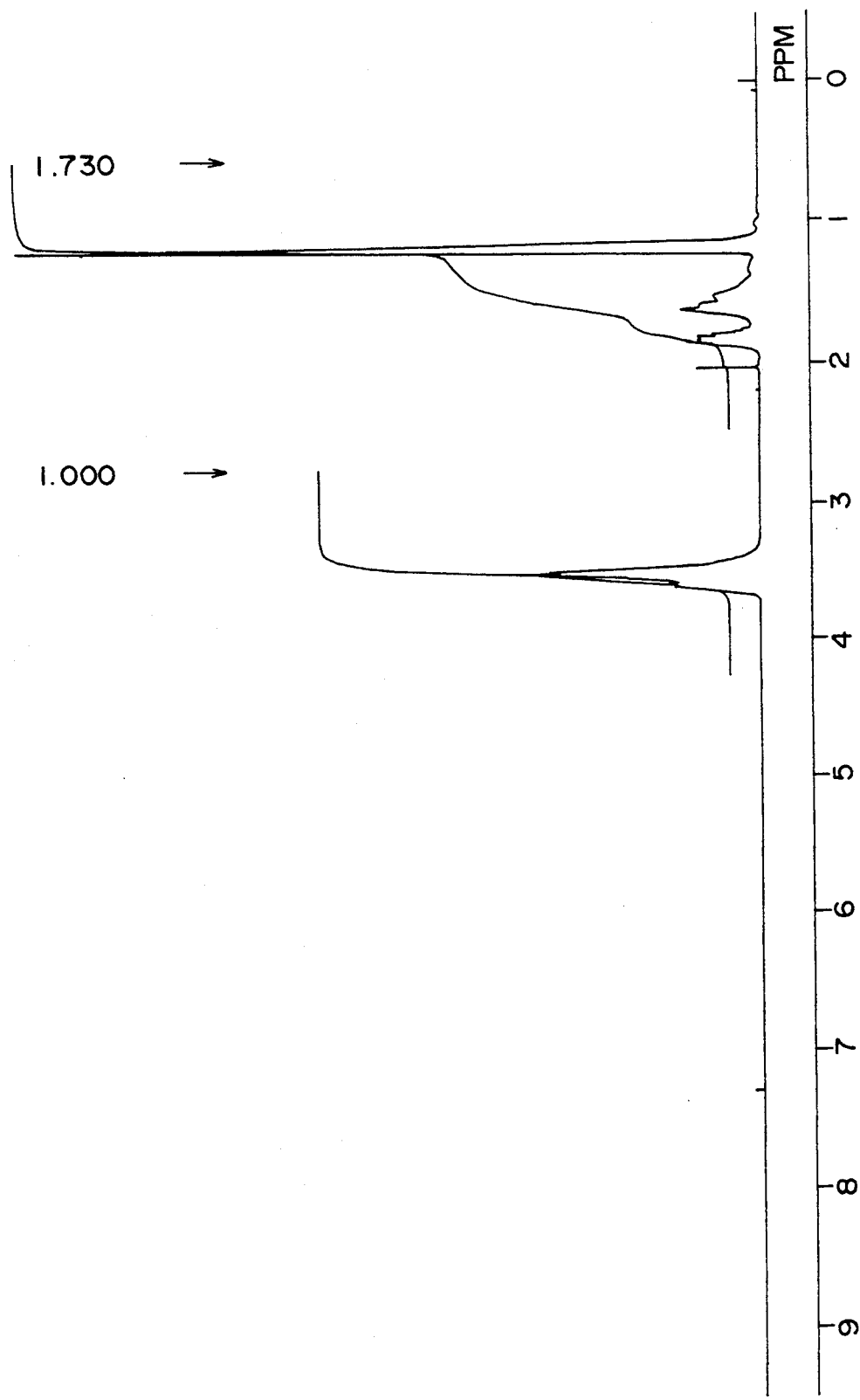
Figure 11:
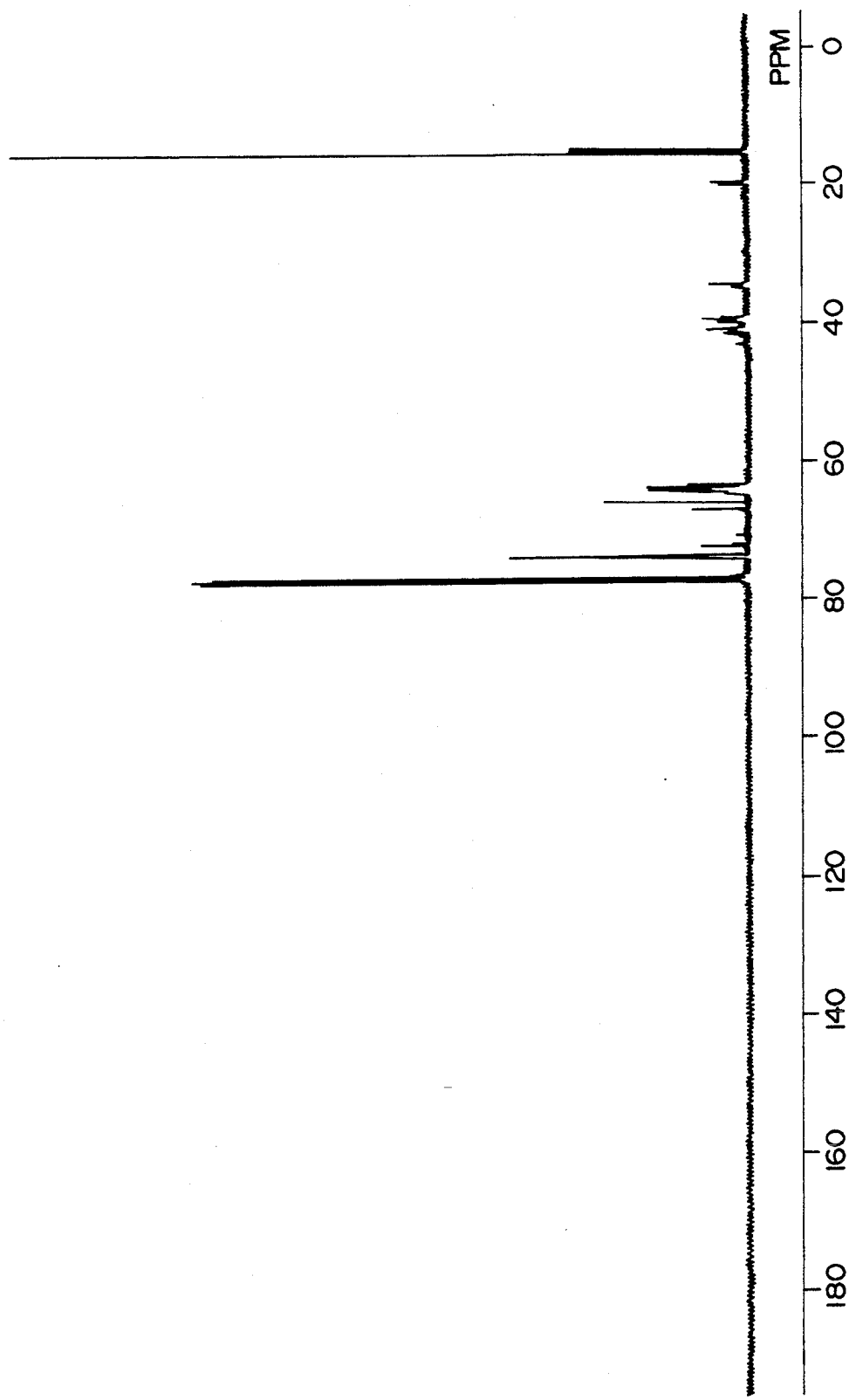

The infrared absorption spectrum is shown in FIG. 9, the $^1$H-NMR chart is shown in FIG. 10 and the $^{13}$C-NMR chart is shown in FIG. 11.

By the same reason as that described in Example 10, the polymer obtained above did not contain any of an unsaturated bond, an acetal structure and an aldehyde structure.

Example 13

(1) Preparation of Polymer of Isopropyl Vinyl Ether

Into a 500 ml glass flask equipped with a dropping funnel, a cooler and a stirrer, 95 g of toluene, 14.7 g of isopropyl alcohol and 1.8 g of boron trifluoride diethyl etherate were charged. Into a dropping funnel, 190 g of isopropyl vinyl ether was charged and dropped in 30 minutes. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 70 ml of a 5 weight % aqueous solution of sodium hydroxide 3 times and then with 70 ml of water 3 times. The solvent and unreacted materials were removed under the reduced pressure by using a rotary evaporator to obtain 179 g of the crude product. The crude product had the kinematic viscosity of 27.0 cSt at 40° C.

Into a 1 liter autoclave made of SUS-316L, 171 g of the crude product, 130 g of hexane, 20 g of Raney nickel prepared in Example of Catalyst Preparation 1 and 20 g of zeolite prepared in Example of Catalyst Preparation 2 were charged. Hydrogen was introduced into the autoclave and the pressure of hydrogen was adjusted to 20 kg/cm². After stirring for about 30 seconds, the pressure was released. Hydrogen was introduced into the autoclave again to make the pressure of hydrogen 20 kg/cm² and, after stirring for about 30 seconds, the pressure of hydrogen was released. After repeating this operation once more, the pressure of hydrogen was increased to 50 kg/cm² and the temperature was increased to 130° C. in 30 minutes under stirring. The reaction was conducted at 130° C. for 1 hour. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm² during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a 2 liter washing vessel and washed with 50 ml of a 5 weight % aqueous solution of sodium hydroxide 3 times and then with 50 ml of distilled water 5 times. Hexane, water and the like were removed under the reduced pressure by using a rotary evaporator. The yield was 131 g.

(2) Evaluation

Kinematic viscosity, average molecular weights and dispersion of molecular weight, compatibility with Flon, volume specific resistance and resistance to hydrolysis of the isopropyl vinyl ether polymer obtained in (1) described above were measured. The results of the measurements are shown in Table 1.

Figure 12:
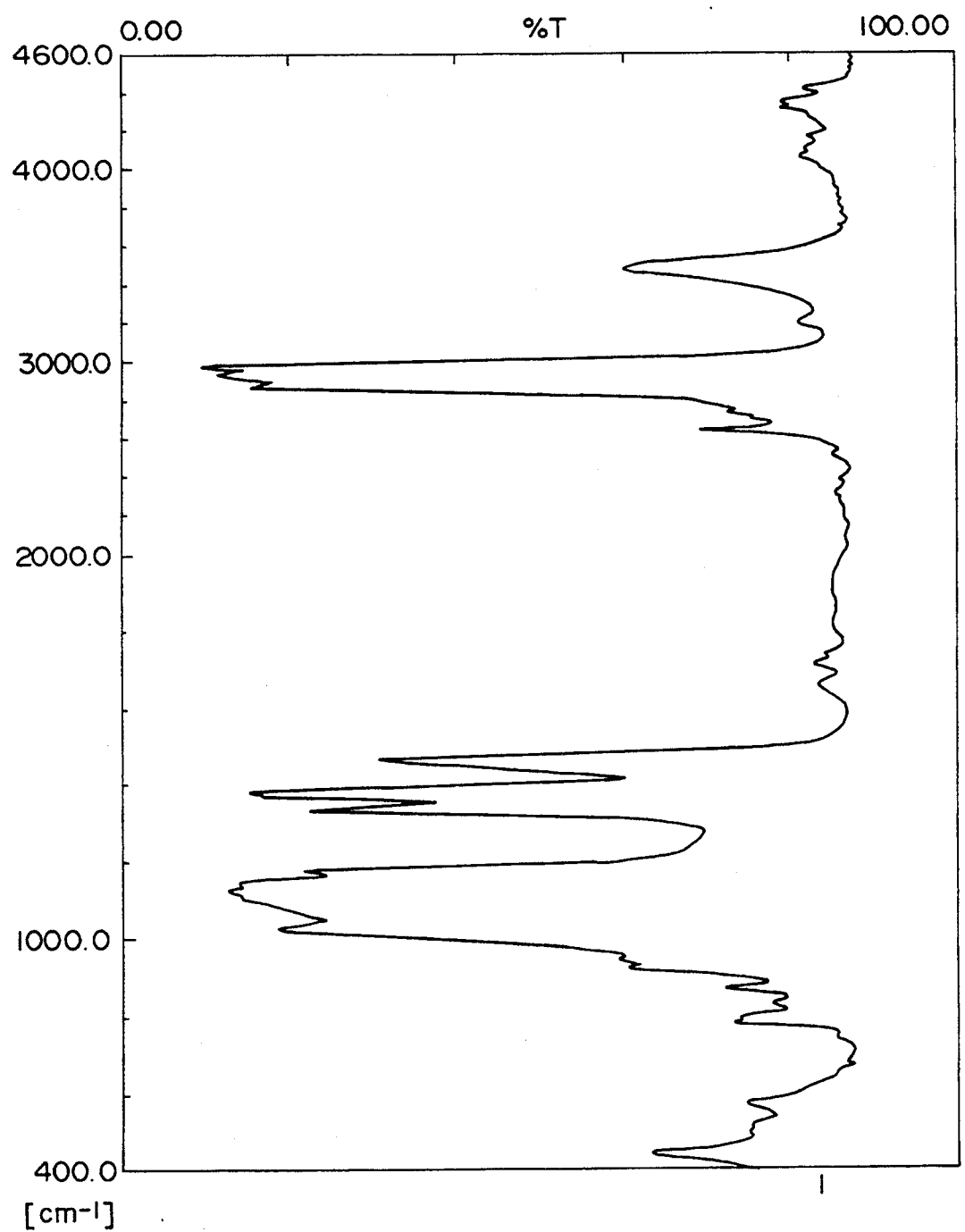
Figure 13:
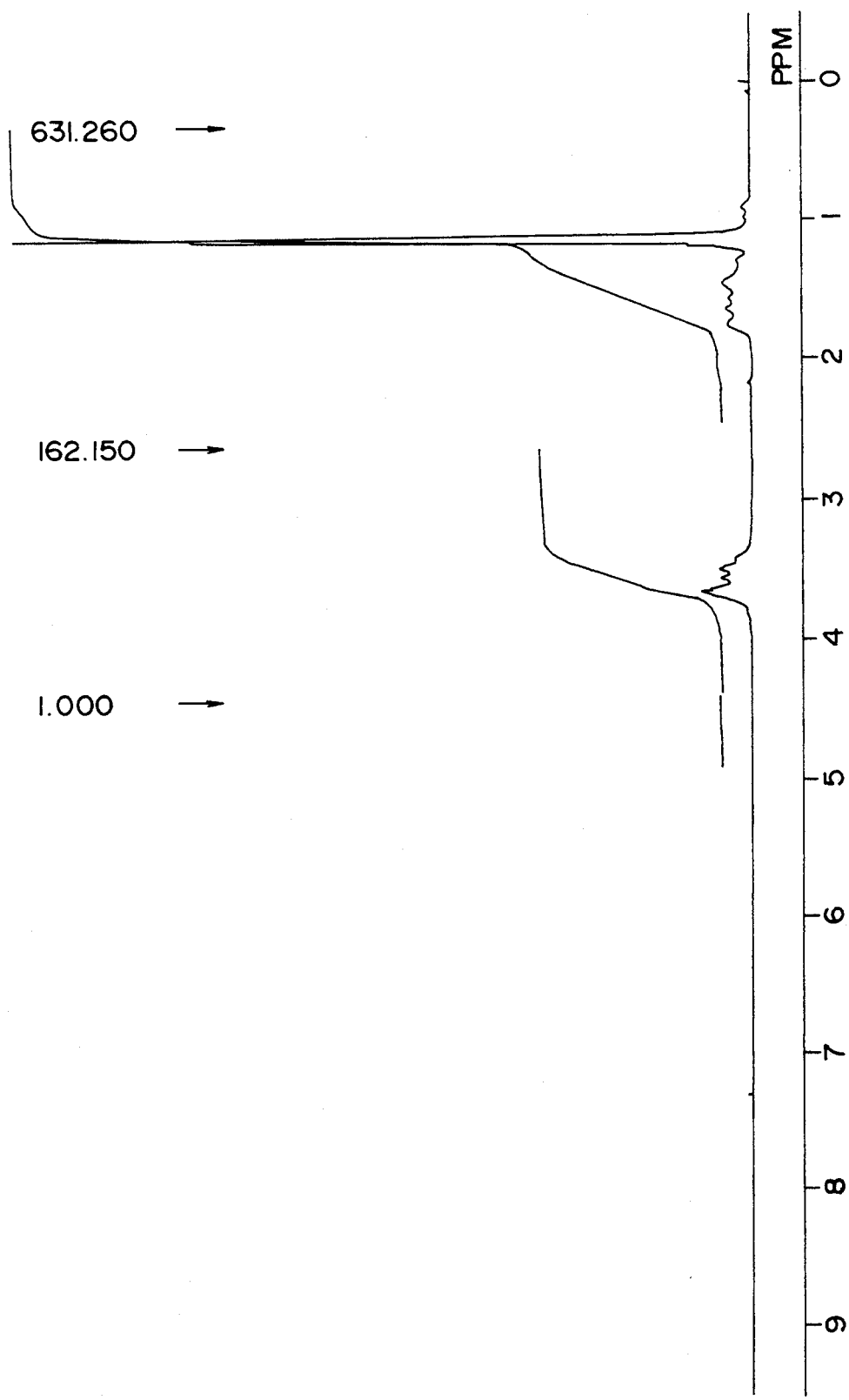
Figure 14:
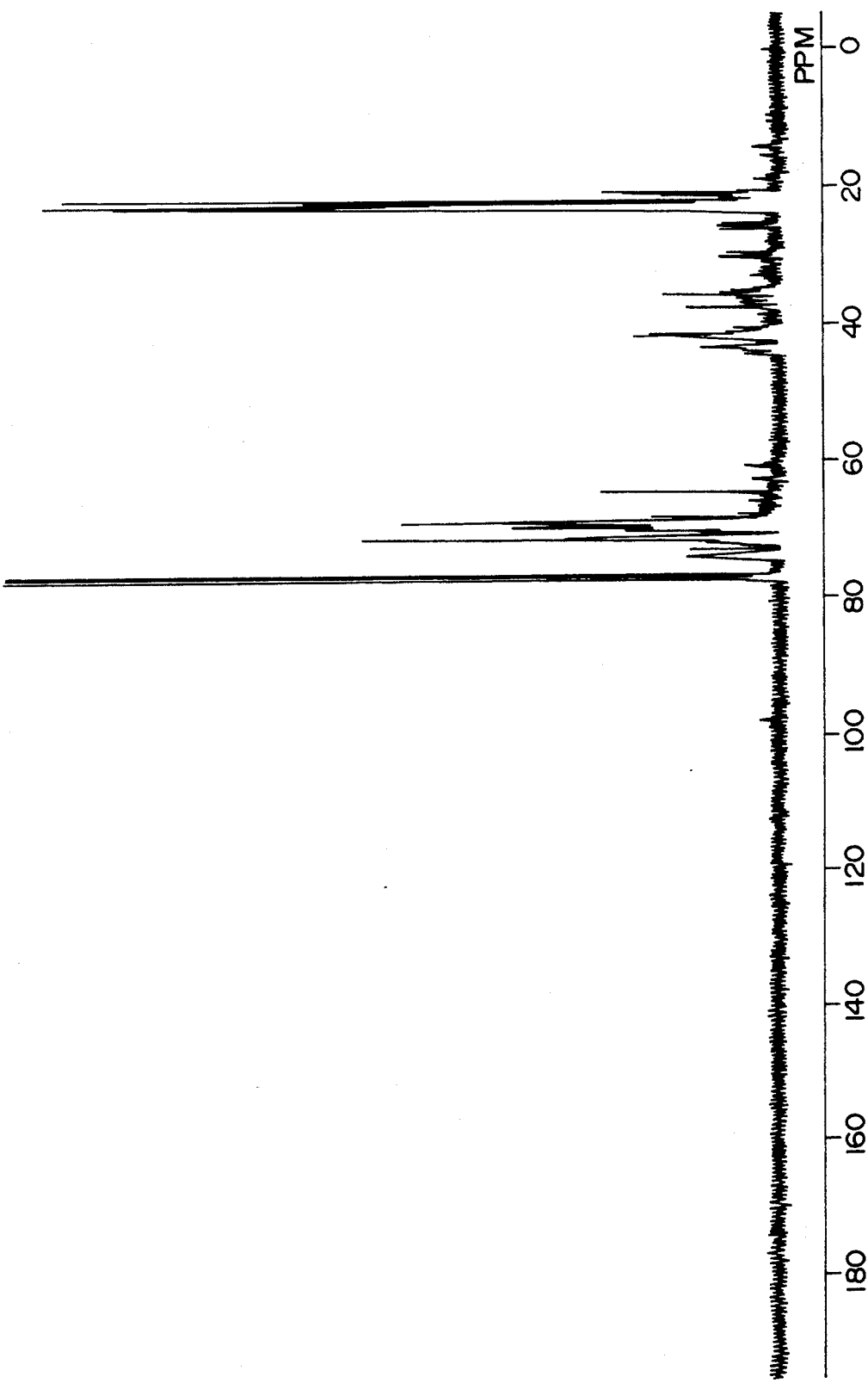

The infrared absorption spectrum is shown in FIG. 12, the $^1$H-NMR chart is shown in FIG. 13 and the $^{13}$C-NMR chart is shown in FIG. 14.

By the same reason as that described in Example 10, the polymer obtained above did not contain any of an unsaturated bond, an acetal structure and an aldehyde structure.

Example 14

(1) Preparation of Polymer of Isopropyl Vinyl Ether

Into a 1 liter glass flask equipped with a dropping funnel, a cooler and a stirrer, 250 g of toluene, 36.82 g of isopropyl alcohol and 4.35 g of boron trifluoride diethyl etherate were charged. Into a dropping funnel, 500 g of isopropyl vinyl ether was charged and dropped in 30 minutes. During this period, the reaction started and the temperature of the reaction solution increased. The temperature was kept at about 30° C. by cooling with an ice water bath. After finishing the dropping, the solution was further stirred for 5 minutes. The reaction mixture was transferred to a washing vessel and washed with 130 ml of a 3 weight % aqueous solution of sodium hydroxide 3 times and then with 200 ml of water 3 times. The solvent and unreacted materials were removed under the reduced pressure by using a rotary evaporator to obtain 475.3 g of the crude product. The crude product had the kinematic viscosity of 32.4 cSt at 40° C.

Into a 1 liter autoclave made of SUS-316L, 380 g of the crude product, 100 g of hexane, 45 g of Raney nickel prepared in Example of Catalyst Preparation 1 and 45 g of zeolite prepared in Example of Catalyst Preparation 2 were charged. Hydrogen was introduced into the autoclave and the pressure of hydrogen was adjusted to 20 kg/cm². After stirring for about 30 seconds, the pressure was released. Hydrogen was introduced into the autoclave again to make the pressure of hydrogen 20 kg/cm² and, after stirring for about 30 seconds, the pressure of hydrogen was released. After repeating this operation once more, the pressure of hydrogen was increased to 50 kg/cm² and the temperature was increased to 130° C. in 30 minutes under stirring. The reaction was conducted at 130° C. for 1 hour and 30 minutes. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm² during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 100 ml of hexane twice. The washing liquid was combined with the reaction liquid and filtered with filter paper. The combined liquid was then transferred to a 2 liter washing vessel and washed with 200 ml of a 5 weight % aqueous solution of sodium hydroxide 3 times and then with 200 ml of distilled water 5 times. Hexane, water and the like were removed under the reduced pressure by using a rotary evaporator. The yield was 287 g.

(2) Evaluation

Kinematic viscosity, average molecular weights and dispersion of molecular weight, compatibility with Flon, volume specific resistance and resistance to hydrolysis of the isopropyl vinyl ether polymer obtained in (1) described above were measured. The results of the measurements are shown in Table 1.

Figure 15:
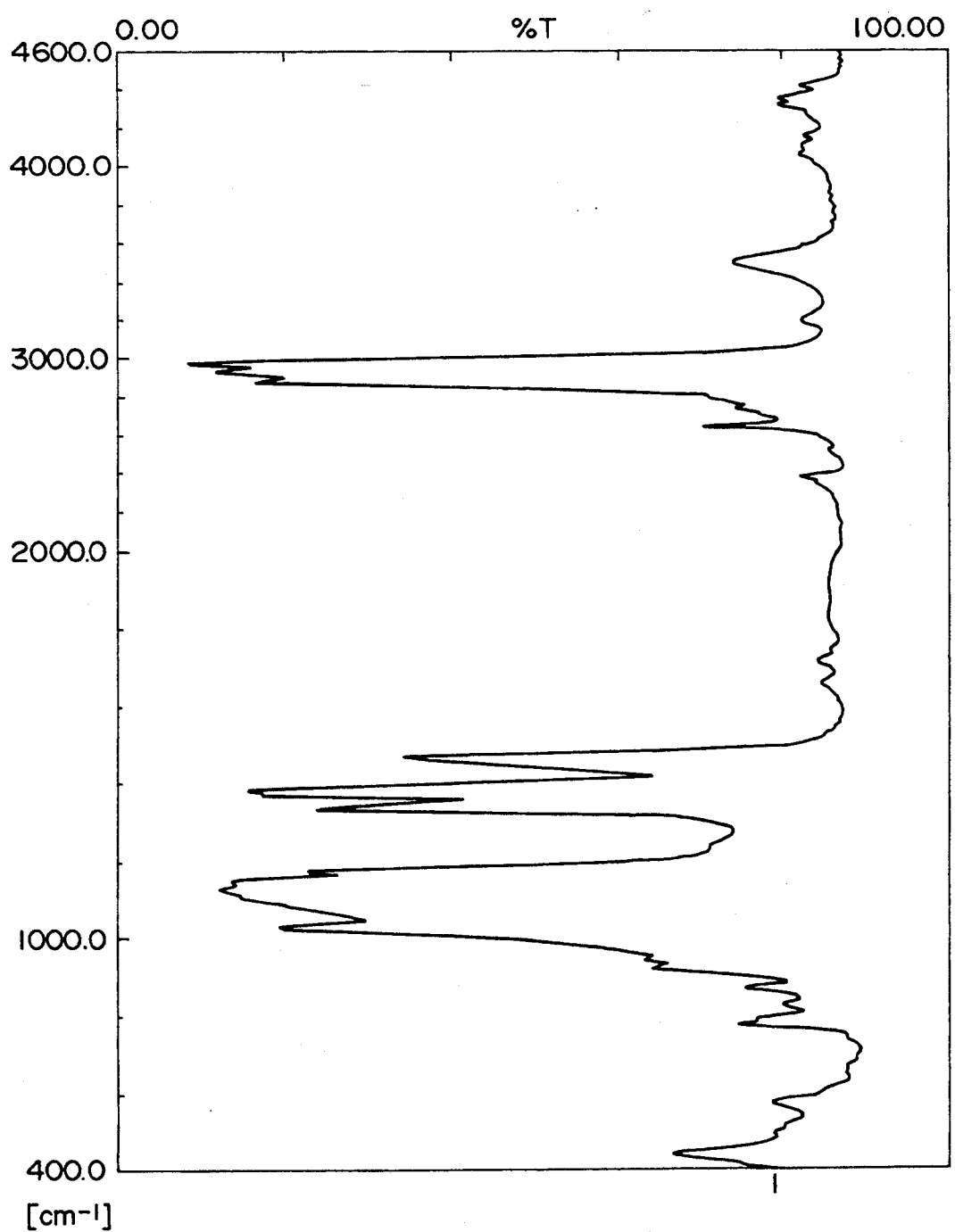

The infrared absorption spectrum is shown in FIG. 15.

By the same reason as that described in Example 10, the polymer obtained above did not contain any of an unsaturated bond, an acetal structure and an aldehyde structure.

Example 15

(1) Preparation of Polymer of Methyl Vinyl Ether

Into a 200 ml stainless steel autoclave equipped with a stirrer, 40 g of toluene, 6.4 g of methanol and 0.45 g of boron trifluoride diethyl etherate were charged. The autoclave was tightly closed and the atmosphere in the autoclave was replaced with nitrogen. Into the autoclave, 107 g of methyl vinyl ether was added from a bomb by the pressure of the compound in 5 hours. The temperature of the reaction solution increased by the heat of reaction and the temperature was kept at about 25° C. by cooling with an ice water bath. After finishing the addition, the solution was further stirred for 10 minutes. The reaction mixture was transferred to a washing vessel and washed with 100 ml of a 5 weight % aqueous solution of sodium hydroxide 3 times and then with 150 ml of water 3 times. The solvent and unreacted materials were removed under the reduced pressure by using a rotary evaporator to obtain 95 g of the crude product. The crude product had the kinematic viscosity of 56.9 cSt at 40° C.

Into a 1 liter autoclave made of SUS-316L, 90 g of the crude product, 300 g of hexane, 4.5 g of Raney nickel and 4.5 g of zeolite were charged. Hydrogen was introduced into the autoclave and the pressure of hydrogen was adjusted to 20 kg/cm². After stirring for about 30 seconds, the pressure was released. Hydrogen was introduced into the autoclave again to make the pressure of hydrogen 20 kg/cm² and, after stirring for about 30 seconds, the pressure of hydrogen was released. After repeating this operation once more, the pressure of hydrogen was increased to 50 kg/cm² and the temperature was increased to 130° C. in 30 minutes under stirring. The reaction was conducted at 130° C. for 1 hour. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm² during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 30 ml of hexane twice. The washing liquid was combined with the reaction liquid and filtered with filter paper. After hexane was removed under the reduced pressure by using a rotary evaporator, 100 ml of toluene was added to the residual product and the product was then transferred to a washing vessel and washed with 100 ml of a 5 weight % aqueous solution of sodium hydroxide 3 times and then with 150 ml of distilled water 5 times. Toluene, water and the like were removed under the reduced pressure by using a rotary evaporator. The yield was 80.5 g.

(2) Evaluation

Kinematic viscosity, average molecular weights and dispersion of molecular weight, compatibility with Flon, volume specific resistance and resistance to hydrolysis of the methyl vinyl ether polymer obtained in (1) described above were measured. The results of the measurements are shown in Table 1.

Figure 16:
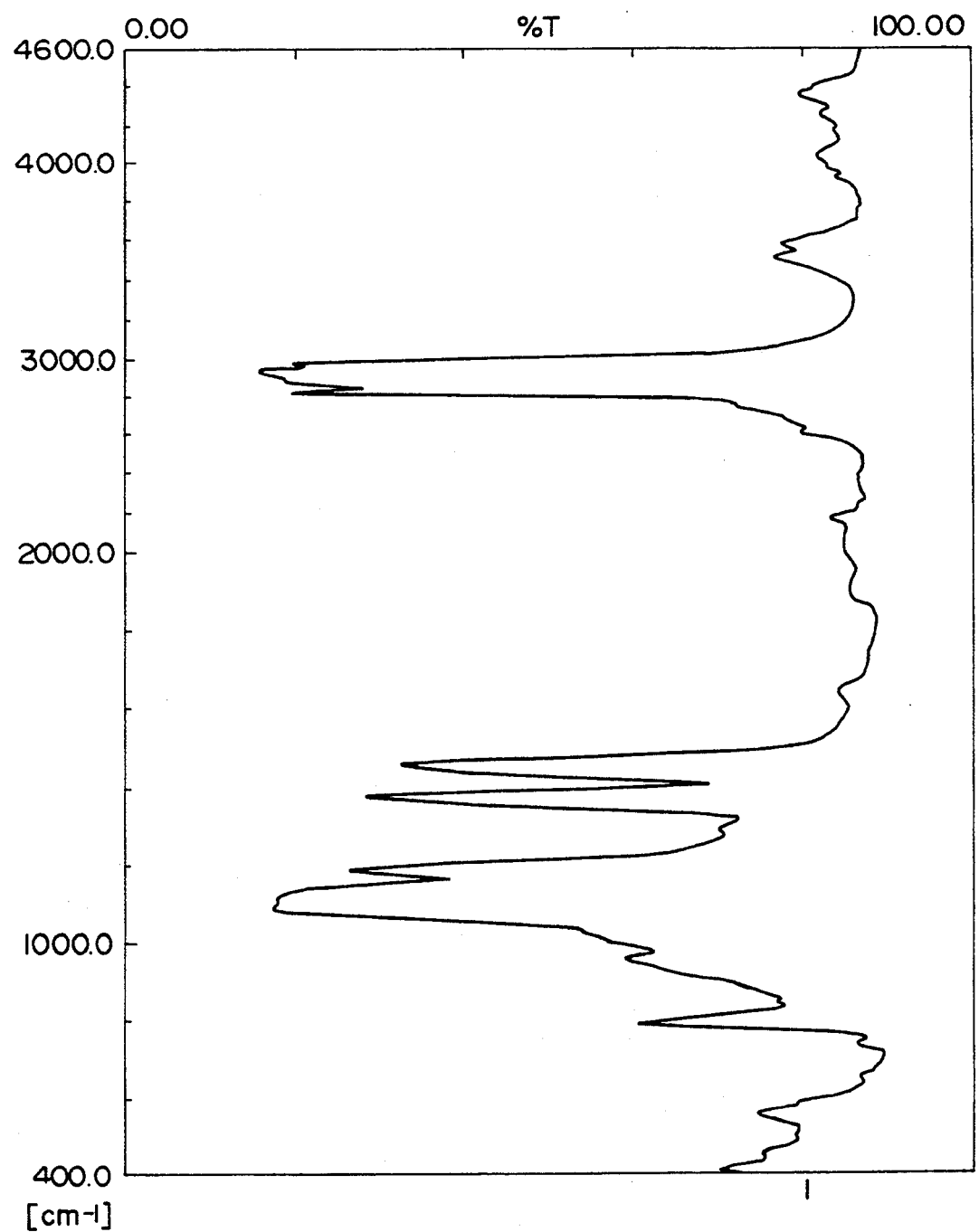
Figure 17:
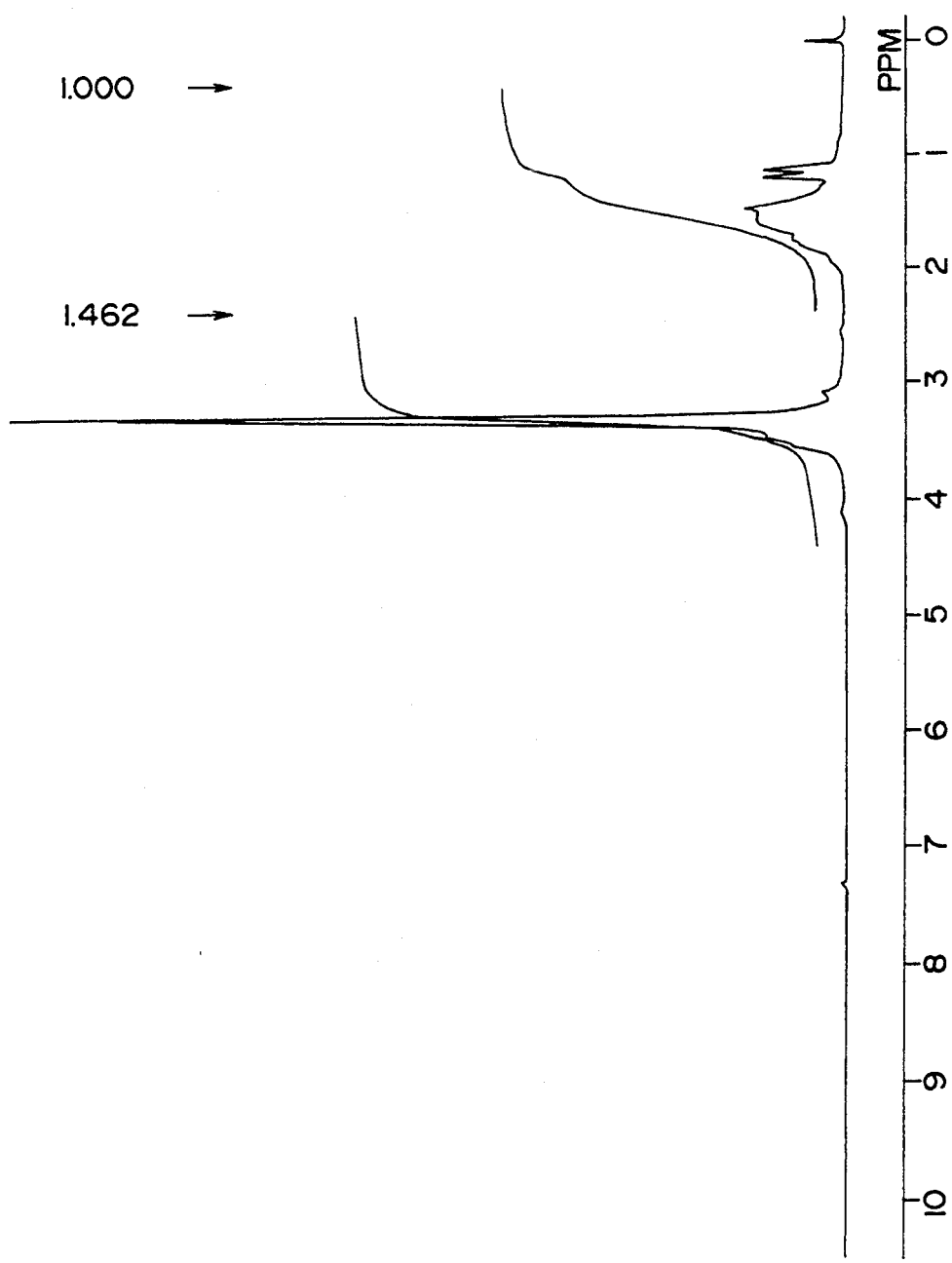
Figure 18:
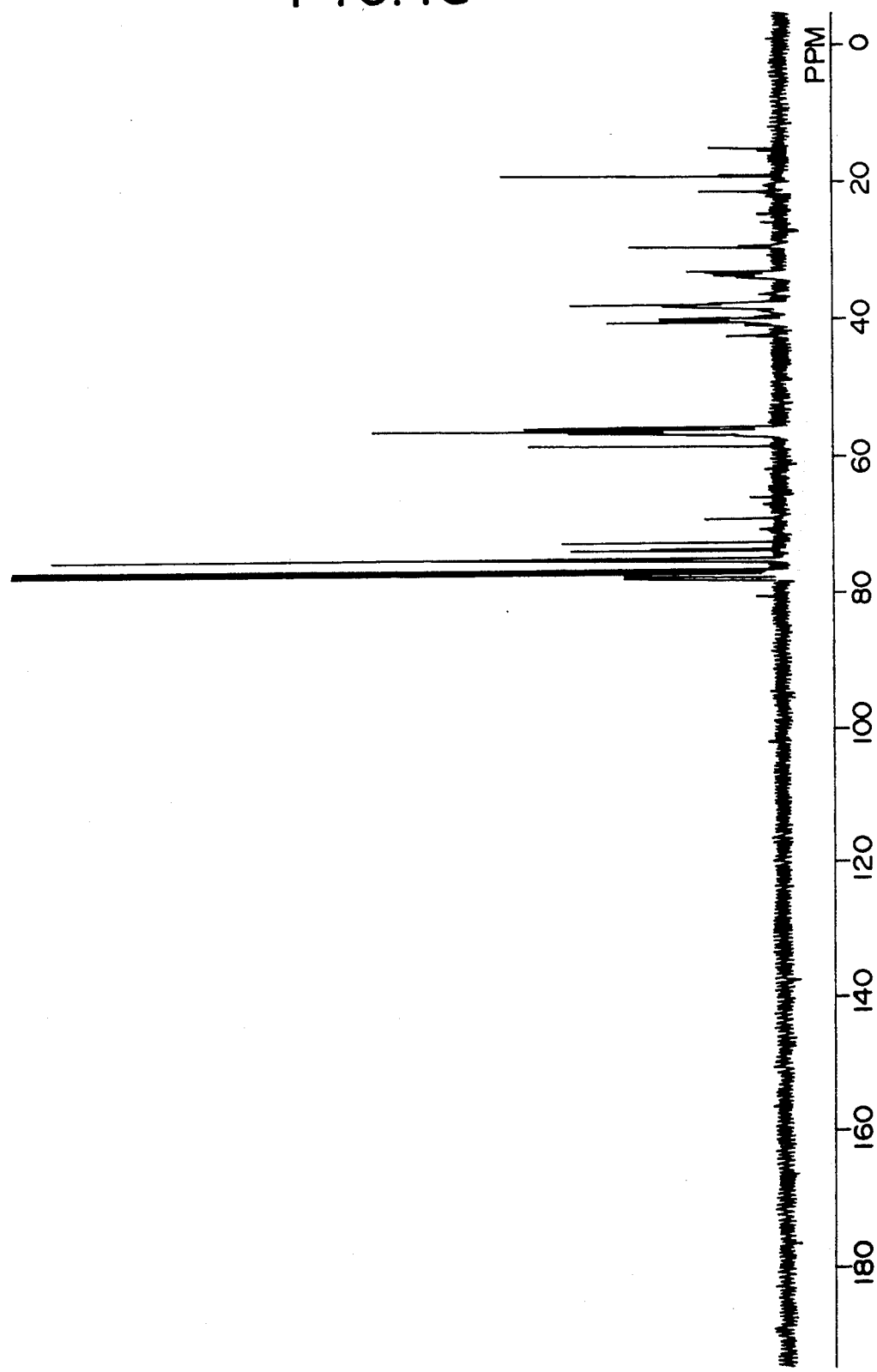

The infrared absorption spectrum is shown in FIG. 16, the $^1$H-NMR chart is shown in FIG. 17 and the $^{13}$C-NMR chart is shown in FIG. 18.

By the same reason as that described in Example 10, the polymer obtained above did not contain any of an unsaturated bond, an acetal structure and an aldehyde structure.

Example 16

(1) Preparation of Copolymer of Ethyl Vinyl Ether and Isopropyl Vinyl Ether

Into a 500 ml glass flask equipped with a dropping funnel, a cooler and a stirrer, 50 g of toluene, 17.7 g of acetaldehyde diethyl acetal and 1.5 g of boron trifluoride diethyl etherate were charged. Into a dropping funnel, 43 g of ethyl vinyl ether and 65 g of isopropyl vinyl ether were charged and dropped in 50 minutes. The temperature of the reaction solution increased by the heat of reaction and the temperature was kept at about 30° C. by cooling with an ice water bath. After finishing the dropping, the solution was further stirred for 5 minutes. The reaction mixture was transferred to a washing vessel and washed with 100 ml of a 5 weight % aqueous solution of sodium hydroxide 3 times and then with 150 ml of water 3 times. The solvent and unreacted materials were removed under the reduced pressure by using a rotary evaporator to obtain 120 g of the crude product. The crude product had the kinematic viscosity of 48.8 cSt at 40° C.

Into a 1 liter autoclave made of SUS-316L, 110 g of the crude product, 300 g of hexane, 5.5 g of Raney nickel and 5.5 g of zeolite were charged. Hydrogen was introduced into the autoclave and the pressure of hydrogen was adjusted to 20 kg/cm². After stirring for about 30 seconds, the pressure was released. Hydrogen was introduced into the autoclave again to make the pressure of hydrogen 20 kg/cm² and, after stirring for about 30 seconds, the pressure of hydrogen was released. After repeating this operation once more, the pressure of hydrogen was increased to 50 kg/cm² and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm² during the reaction. After finishing the reaction, the reaction mixture was cooled to the room temperature and the pressure was decreased to the atmospheric pressure. The reaction liquid was removed by decantation. The catalyst was washed with 30 ml of hexane twice. The washing liquid was combined with the reaction liquid and filtered with filter paper. The filtered combined liquid is then transferred to a washing vessel and washed with 100 ml of a 5 weight % aqueous solution of sodium hydroxide 3 times and then with 150 ml of distilled water 5 times. Hexane, water and the like were removed under the reduced pressure by using a rotary evaporator. The yield was 97 g.

(2) Evaluation

Kinematic viscosity, average molecular weights and dispersion of molecular weight, compatibility with Flon, volume specific resistance and resistance to hydrolysis of the ethyl vinyl ether/isopropyl vinyl ether copolymer obtained in (1) described above were measured. The results of the measurements are shown in Table 1.

Figure 19:
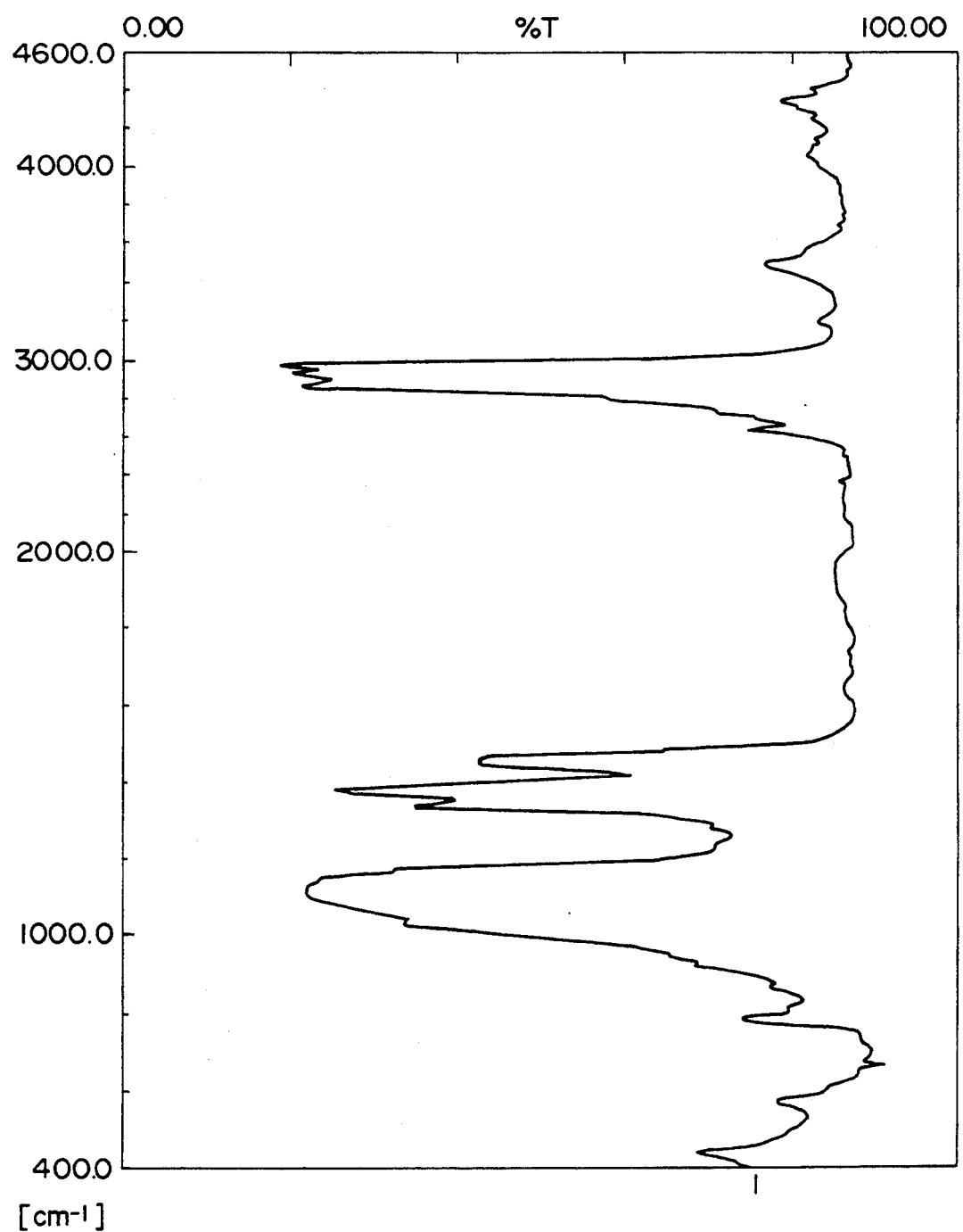
Figure 20:
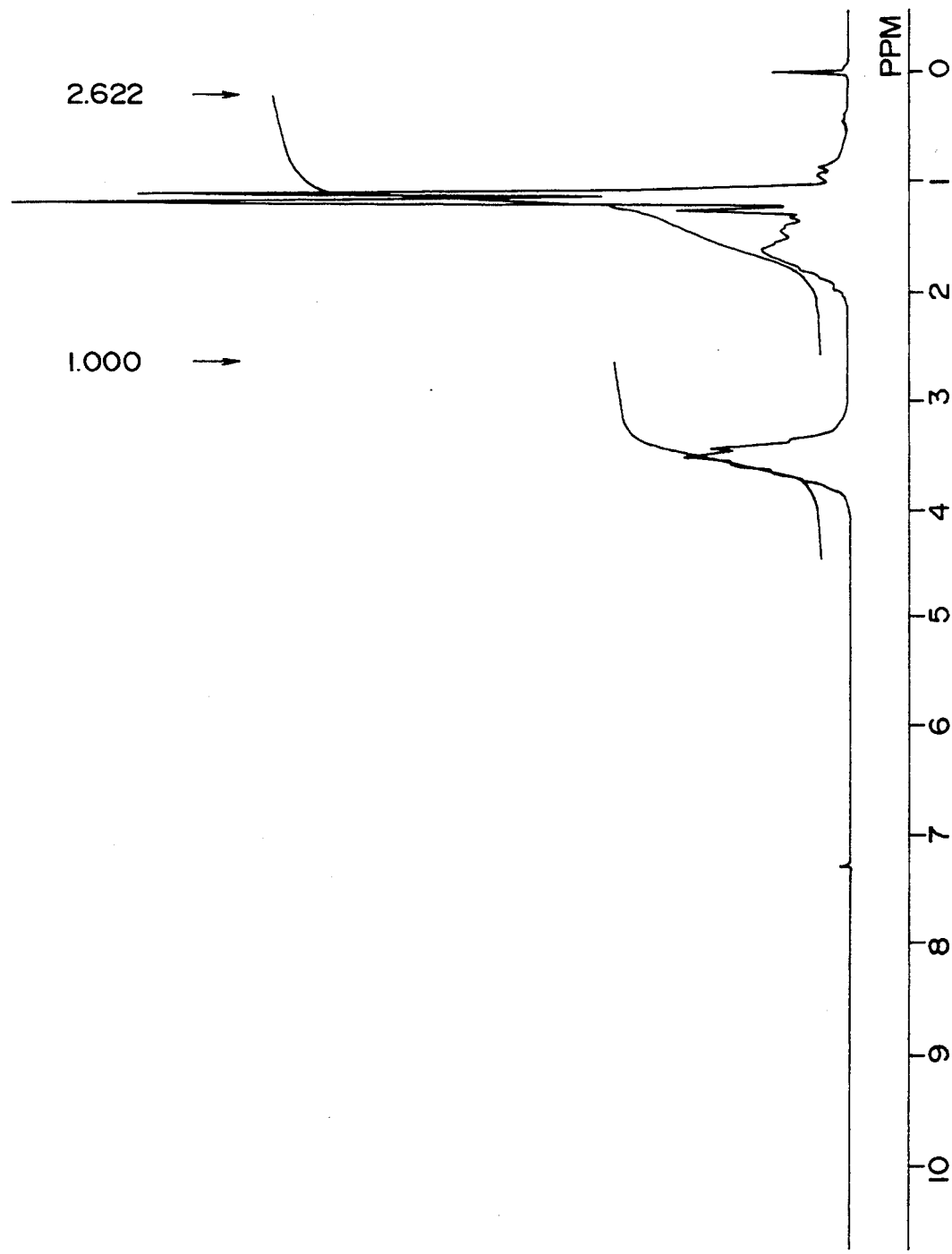
Figure 21:
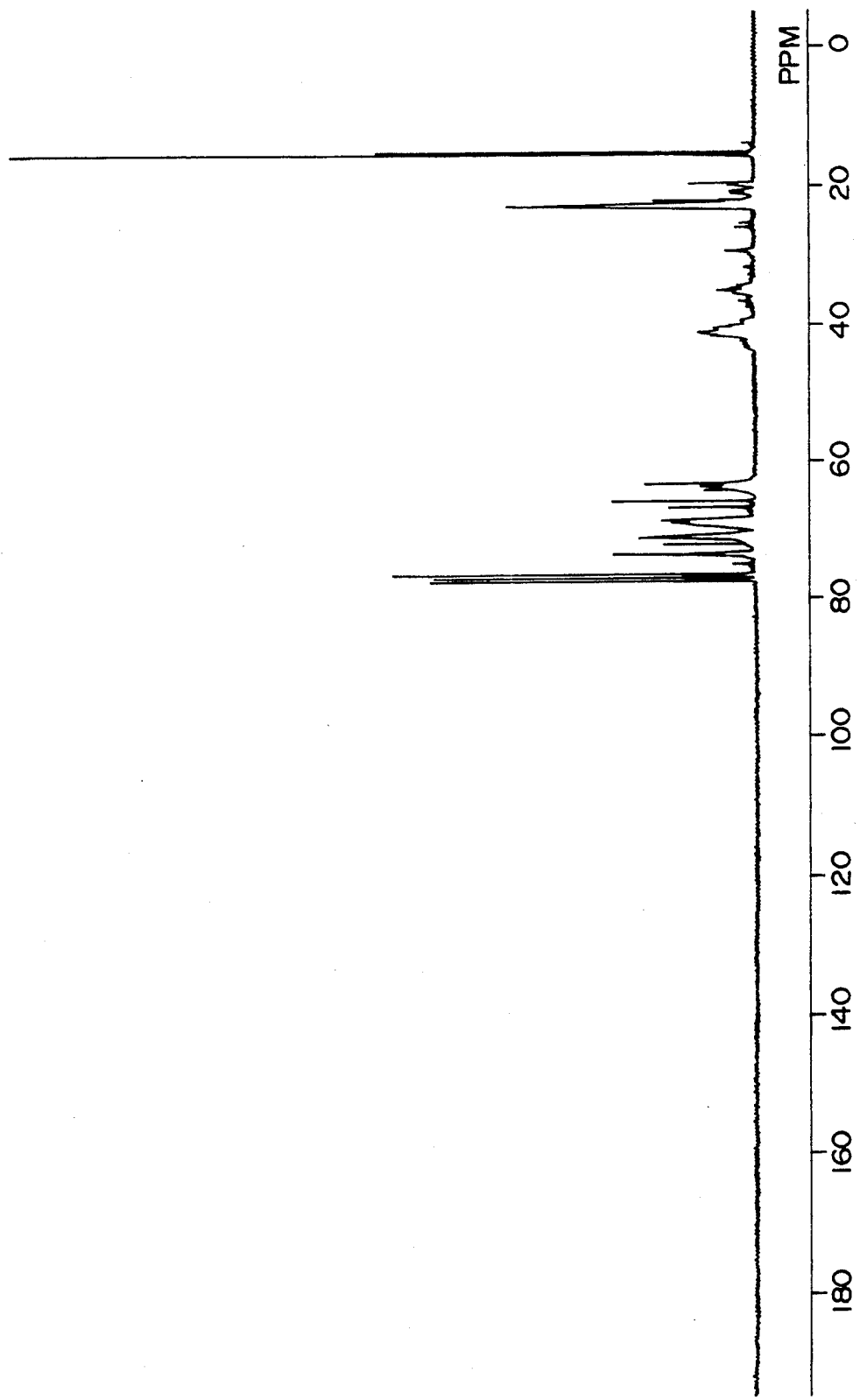

The infrared absorption spectrum is shown in FIG. 19, the $^1$H-NMR chart is shown in FIG. 20 and the $^{13}$C-NMR chart are shown in FIG. 21.

By the same reason as that described in Example 10, the copolymer obtained above did not contain any of an unsaturated bond, an acetal structure and an aldehyde structure.

Example 17

(1) Preparation of Polymer of Isobutyl Vinyl Ether

Into a 500 ml glass flask equipped with a dropping funnel, a cooler and a stirrer, 50 g of toluene, 11 g of isobutyl alcohol and 0.5 g of boron trifluoride diethyl etherate were charged. Into a dropping funnel, 100 g of isobutyl vinyl ether was charged and dropped in 55 minutes. The temperature of the reaction solution increased by the heat of reaction and the temperature was kept at about 30° C. by cooling with an ice water bath. After finishing the dropping, the solution was further stirred for 5 minutes. The reaction mixture was transferred to a washing vessel and washed with 100 ml of a 5 weight % aqueous solution of sodium hydroxide 3 times and then with 150 ml of water 3 times. The solvent and unreacted materials were removed under the reduced pressure by using a rotary evaporator to obtain 107 g of the crude product. The crude product had the kinematic viscosity of 52.4 cSt at 40° C.

Into a 1 liter autoclave made of SUS-316L, 90 g of the crude product, 300 g of hexane, 4.8 g of Raney nickel and 4.8 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 140° C. in 30 minutes under stirring. The reaction was conducted at 140° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 30 ml of hexane twice. The washing liquid was combined with the reaction liquid and filtered with filter paper.

The combined liquid was then transferred to a 1 liter washing vessel and washed with 100 ml of a 5 weight % aqueous solution of sodium hydroxide 3 times and then with 150 ml of distilled water 5 times. Hexane, water and the like were removed under the reduced pressure by using a rotary evaporator. The yield was 80.5 g.

(2) Evaluation

Kinematic viscosity, average molecular weights and dispersion of molecular weight, compatibility with Flon, volume specific resistance and resistance to hydrolysis of the isobutyl vinyl ether polymer obtained in (1) described above were measured. The results of the measurements are shown in Table 1.

Figure 22:
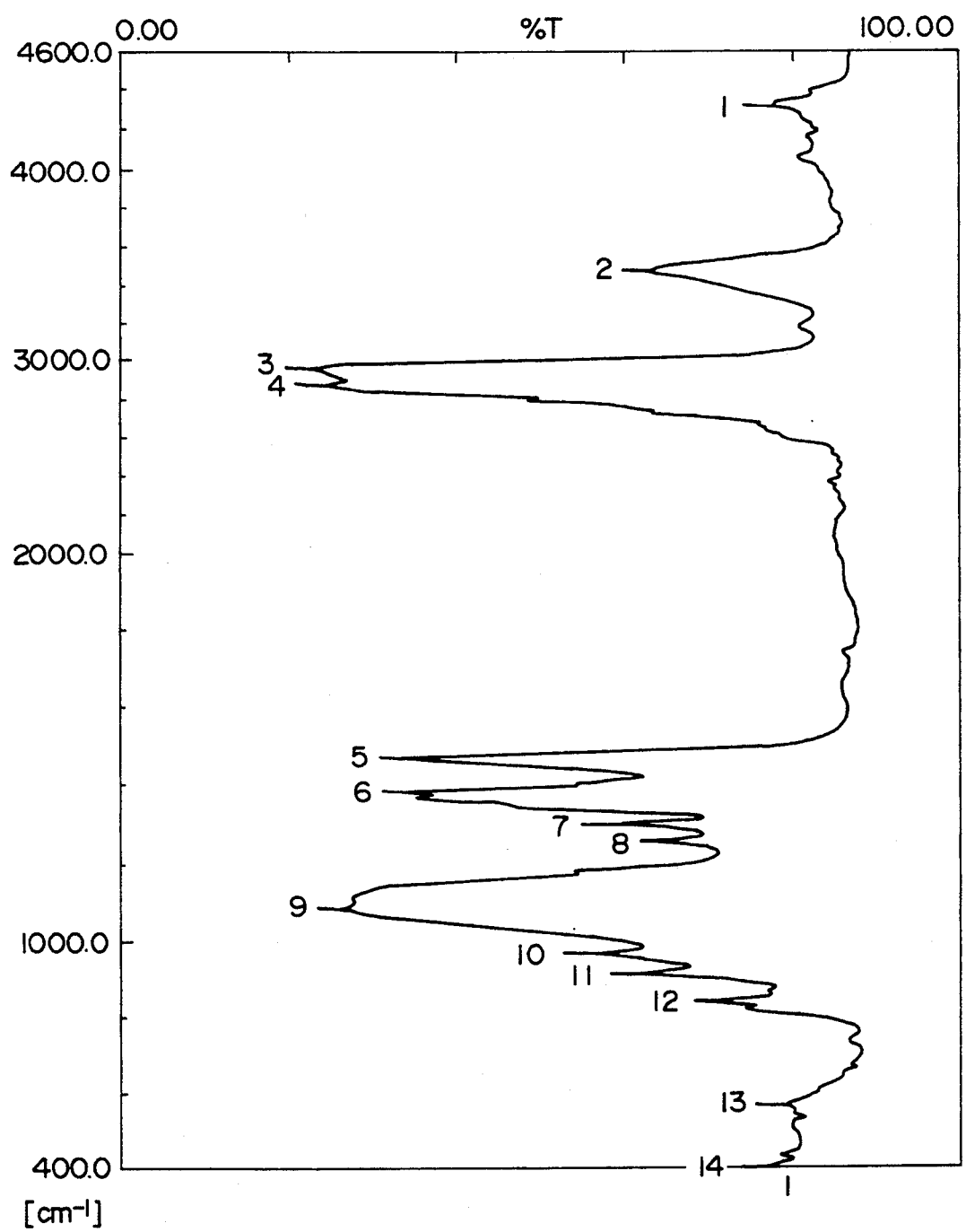
Figure 23:
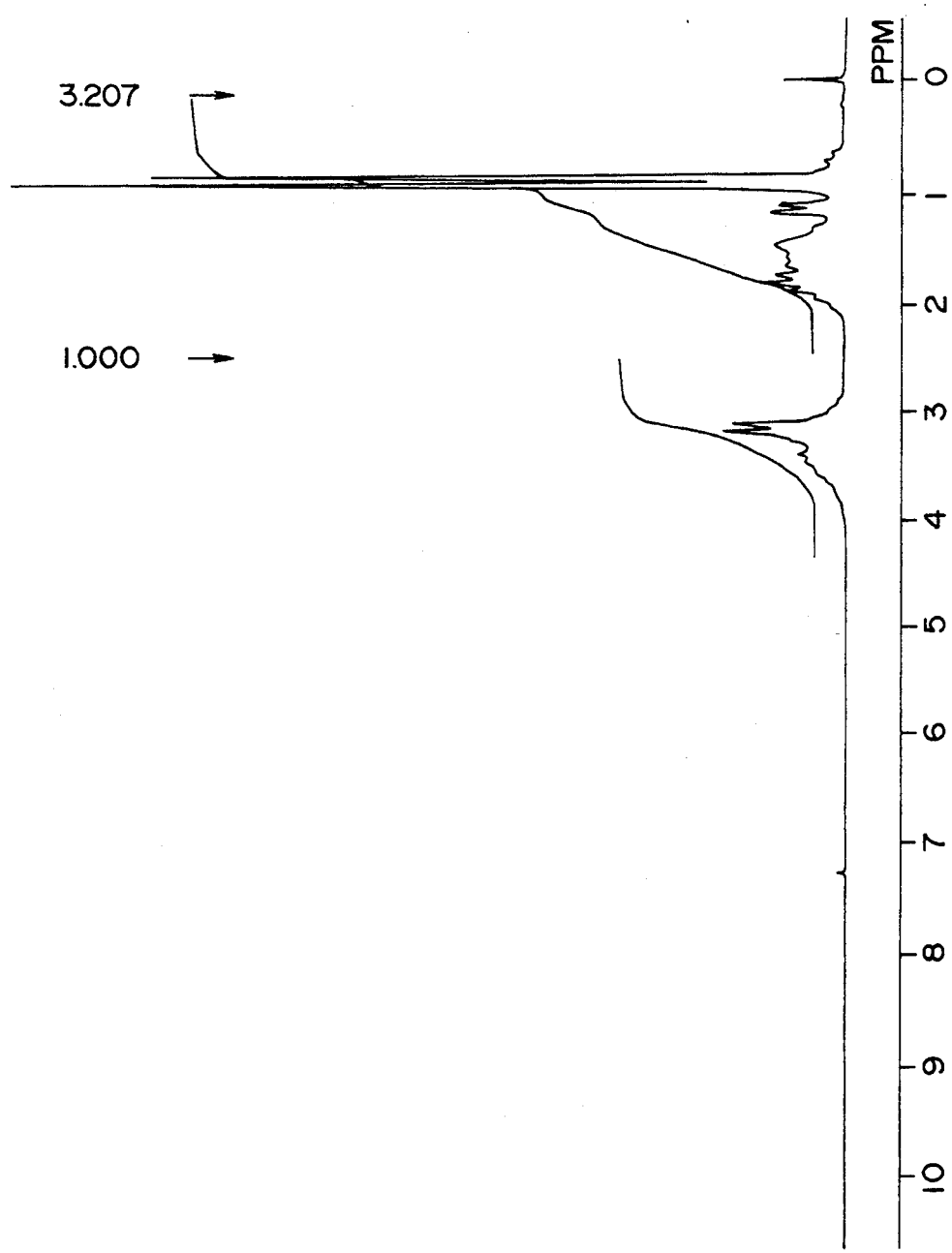
Figure 24:
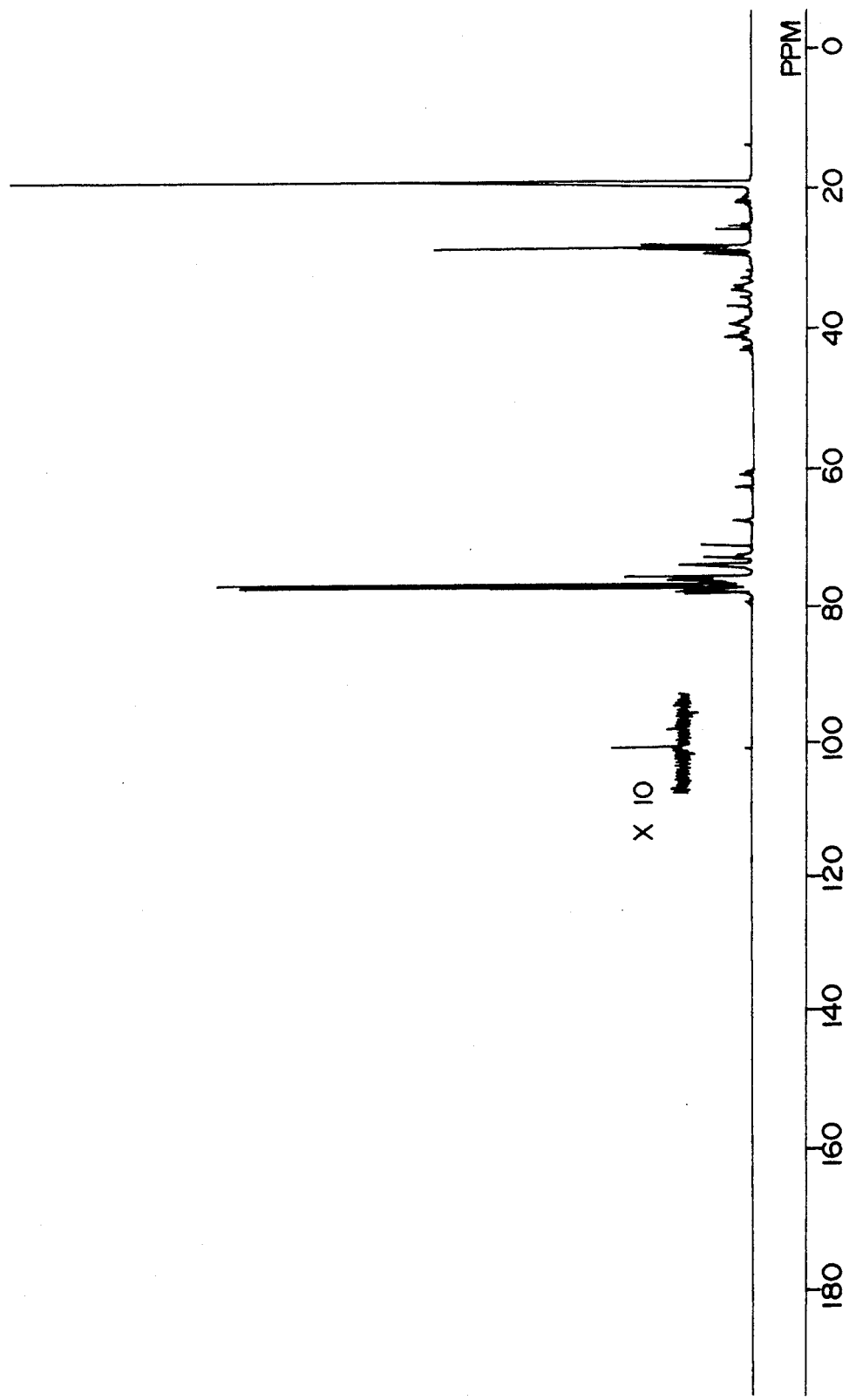

The infrared absorption spectrum is shown in FIG. 22, the $^1$H-NMR chart is shown in FIG. 23 and the $^{13}$C-NMR chart is shown in FIG. 24.

By the same reason as that described in Example 10, the polymer obtained above did not contain any of an unsaturated bond, an acetal structure and an aldehyde structure.

Example 18

(1) Preparation of Polymer of 1-Ethoxy-1-propene

Into a 500 ml glass flask equipped with a dropping funnel, a cooler and a stirrer, 80 g of toluene, 40 g of propionaldehyde diethyl acetal and 0.4 g of boron trifluoride diethyl etherate were charged. Into a dropping funnel, 116 g of 1-ethoxy-1-propene was charged and dropped in 60 minutes. The temperature of the reaction solution increased by the heat of reaction and the temperature was kept at about 30° C. by cooling with an ice water bath. After finishing the dropping, the solution was further stirred for 40 minutes. The reaction mixture was transferred to a washing vessel and washed with 150 ml of a 5 weight % aqueous solution of sodium hydroxide 3 times and then with 200 ml of water 3 times. The solvent and unreacted materials were removed under the reduced pressure by using a rotary evaporator to obtain 140 g of the crude product. The crude product had the kinematic viscosity of 34.4 cSt at 40° C.

Into a 1 liter autoclave made of SUS-316L, 120 g of the crude product, 300 g of hexane, 6 g of Raney nickel and 6 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 130° C. in 30 minutes under stirring. The reaction was conducted at 130° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 50 ml of hexane twice. The washing liquid was combined with the reaction liquid and filtered with filter paper.

The combined liquid was then transferred to a 1 liter washing vessel and washed with 150 ml of a 5 weight % aqueous solution of sodium hydroxide 3 times and then with 200 ml of distilled water 5 times. Hexane, water and the like were removed under the reduced pressure by using a rotary evaporator. The yield was 95 g.

(2) Evaluation

Kinematic viscosity, average molecular weights and dispersion of molecular weight, compatibility with Flon, volume specific resistance and resistance to hydrolysis of the 1-ethoxy-1-propene polymer obtained in (1) described above were measured. The results of the measurements are shown in Table 1.

Figure 25:
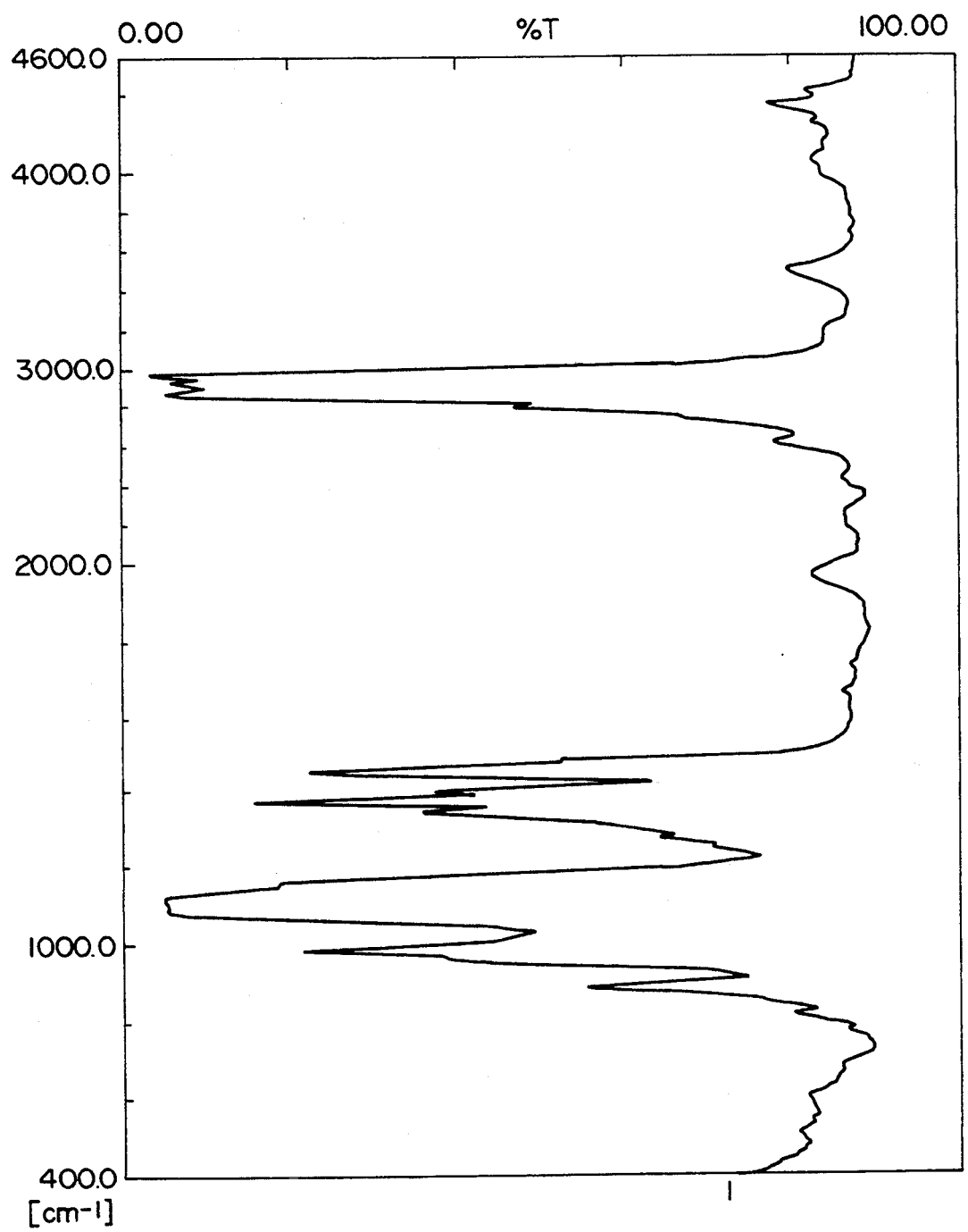
Figure 26:
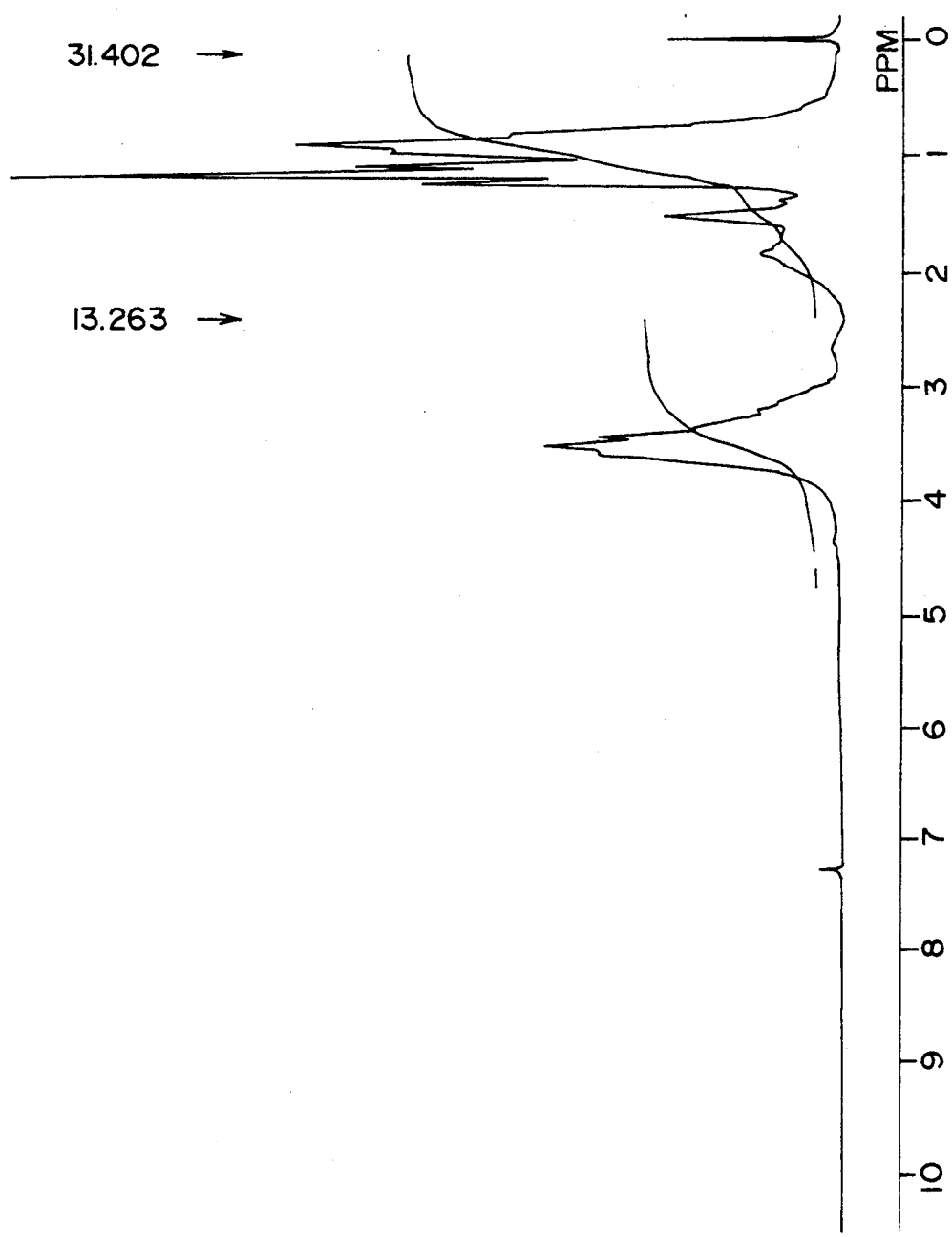
Figure 27:
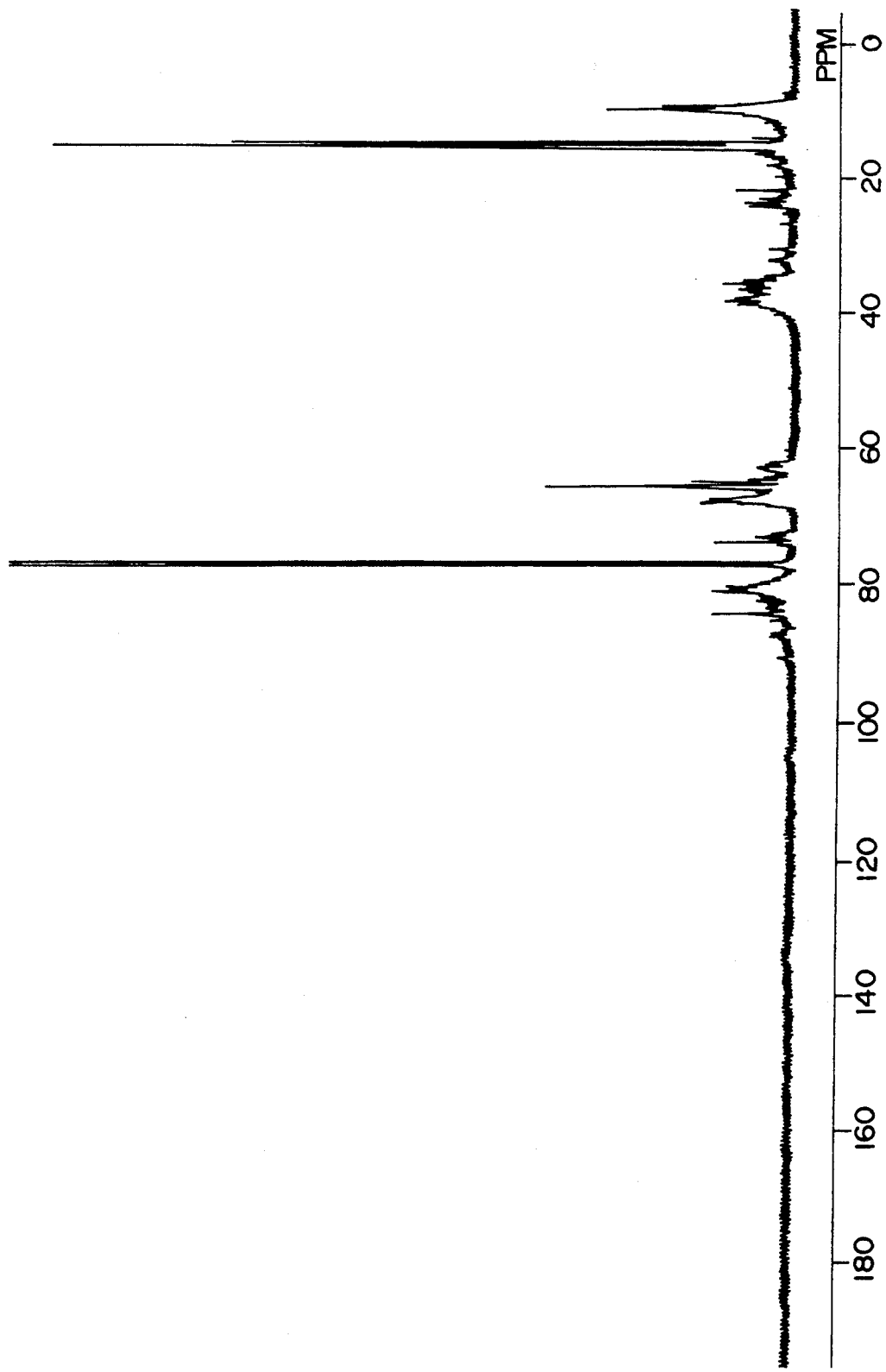

The infrared absorption spectrum is shown in FIG. 25, the $^1$H-NMR chart is shown in FIG. 26 and the $^{13}$C-NMR chart is shown in FIG. 27.

By the same reason as that described in Example 10, the polymer obtained above did not contain any of an unsaturated bond, an acetal structure and an aldehyde structure.

Example 19

(1) Preparation of Polymer of Methoxyethyl Vinyl Ether

Into a 500 ml glass flask equipped with a dropping funnel, a cooler and a stirrer, 100 g of toluene, 21.3 g of acetaldehyde dimethoxyethyl acetal and 0.45 g of boron trifluoride diethyl etherate were charged. Into a dropping funnel, 112 g of methoxyethyl vinyl ether was charged and dropped in 50 minutes. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and 200 ml of chloroform was added to it. The product was washed with 100 ml of a 5 weight % aqueous solution of sodium hydroxide 3 times and then with 150 ml of water 3 times. The solvent and unreacted materials were removed under the reduced pressure by using a rotary evaporator to obtain 129 g of the crude product. The crude product had the kinematic viscosity of 33.3 cSt at 40° C.

Into a 1 liter autoclave made of SUS-316L, 110 g of the crude product, 300 g of hexane, 5.5 g of Raney nickel and 5.5 g of zeolite were charged. Hydrogen was introduced into the autoclave and the pressure of hydrogen was adjusted to 20 kg/cm$^2$. After stirring for about 30 seconds, the pressure was released. Hydrogen was introduced into the autoclave again to make the pressure of hydrogen 20 kg/cm$^2$ and, after stirring for about 30 seconds, the pressure of hydrogen was released. After repeating this operation once more, the pressure of hydrogen was increased to 50 kg/cm$^2$ and the temperature was increased to 130° C. in 30 minutes under stirring. The reaction was conducted at 130° C. for 2 hours. The reaction proceeded during and after the increase of the temperature and decrease of the hydrogen pressure was observed. The increase of the pressure by the increase of the temperature and the decrease of the pressure by the reaction were suitably compensated by decreasing or increasing the pressure and the pressure of hydrogen was kept at 50 kg/cm$^2$ during the reaction. After finishing the reaction, the reaction mixture was cooled to the room temperature and the pressure was decreased to the atmospheric pressure. The catalyst was precipitated by standing for 1 hour and the reaction liquid was separated by decantation. The catalyst was washed with 30 ml of hexane twice. The washing liquid was combined with the reaction liquid and filtered with filter paper. Hexane was removed from the combined liquid under the reduced pressure by using a rotary evaporator and 200 ml of chloroform was added to the remaining product. The product was then transferred to a washing vessel and washed with 100 ml of a 5 weight % aqueous solution of sodium hydroxide 3 times and then with 150 ml of distilled water 5 times. The solvent, water and the like were removed under the reduced pressure by using a rotary evaporator. The yield was 94 g.

(2) Evaluation

Kinematic viscosity, compatibility with Flon and resistance to hydrolysis of the methoxyethyl vinyl ether polymer obtained in (1) described above were measured. The results of the measurements are shown in Table 1.

Figure 28:
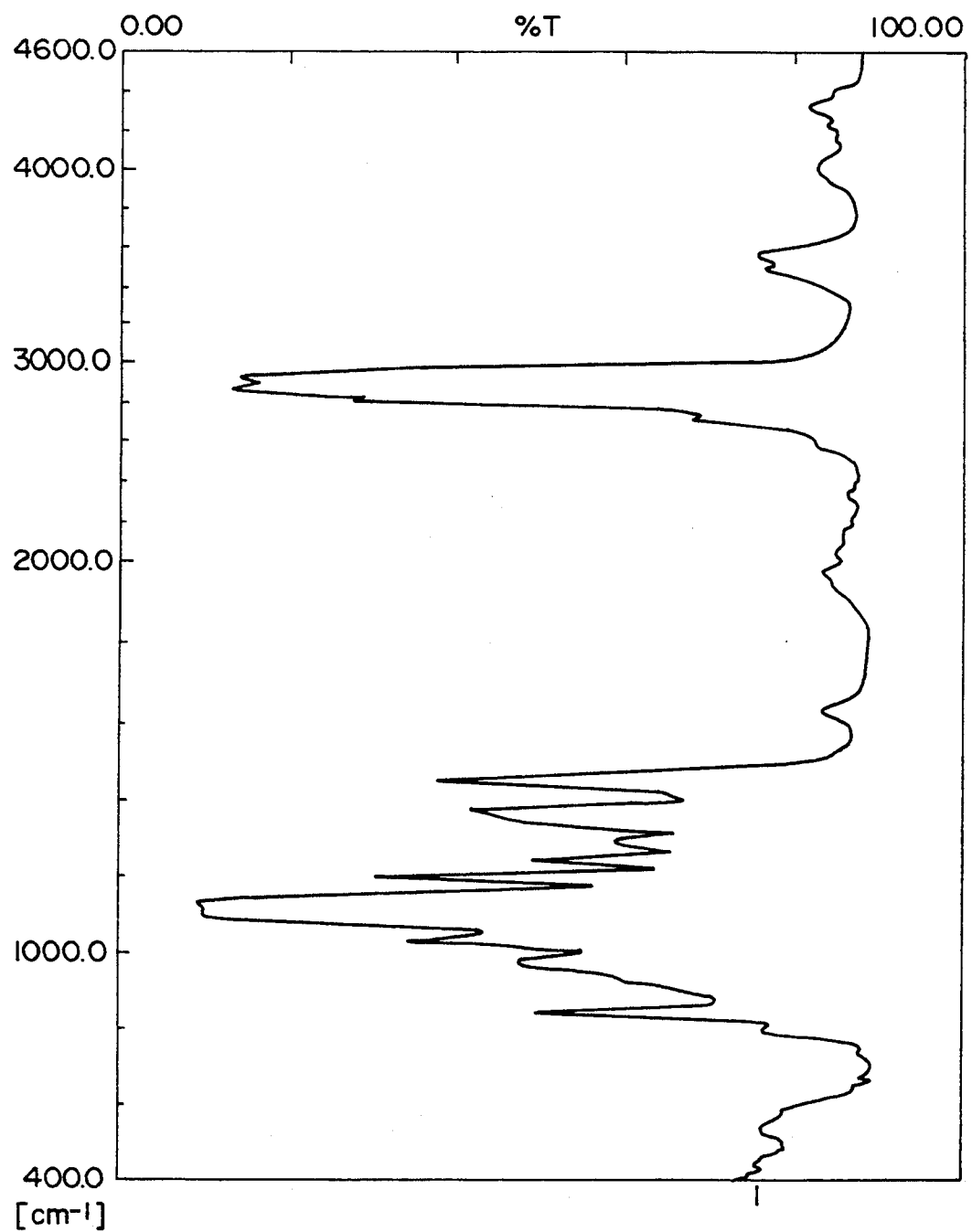
Figure 29:
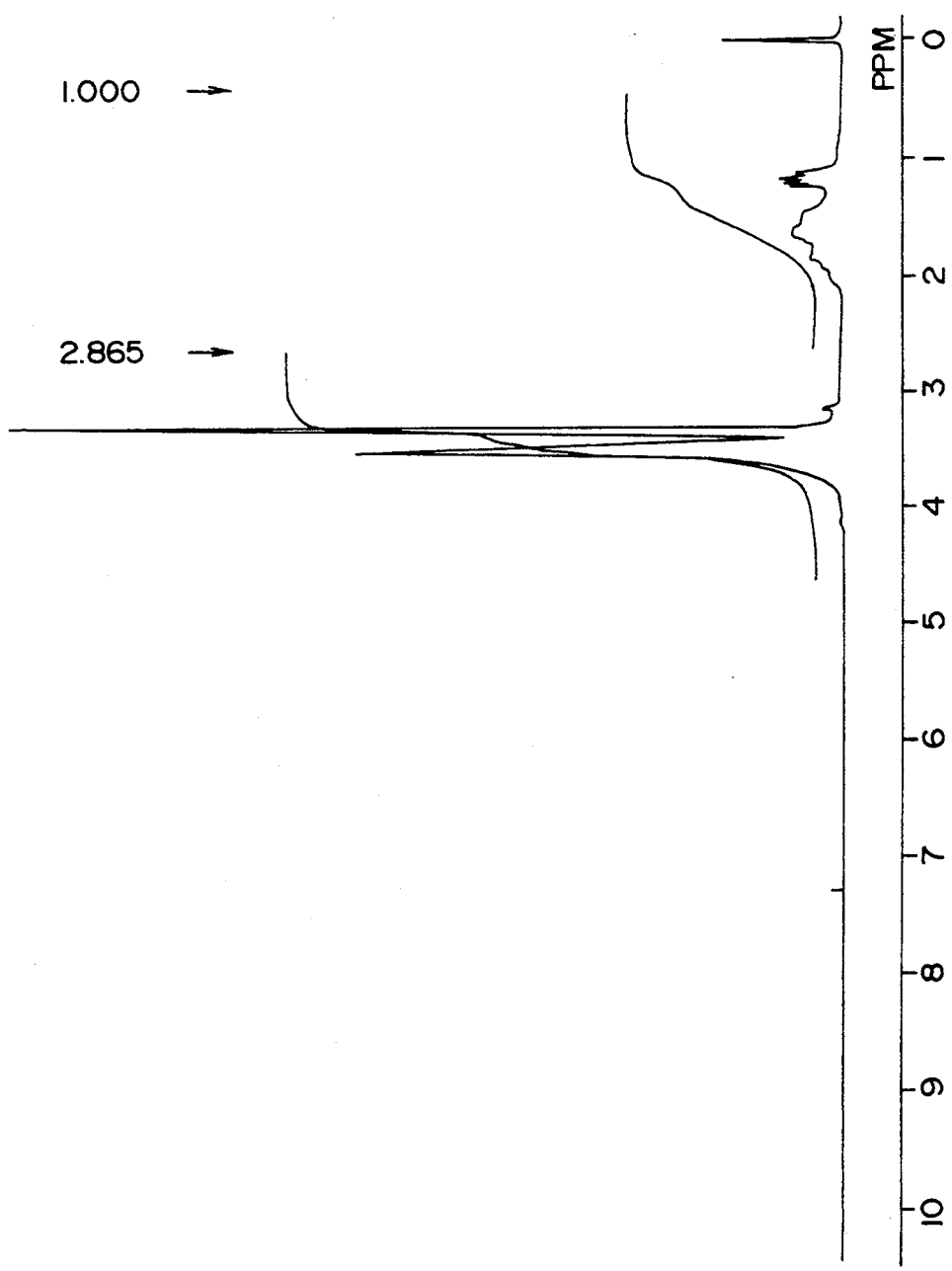
Figure 30:
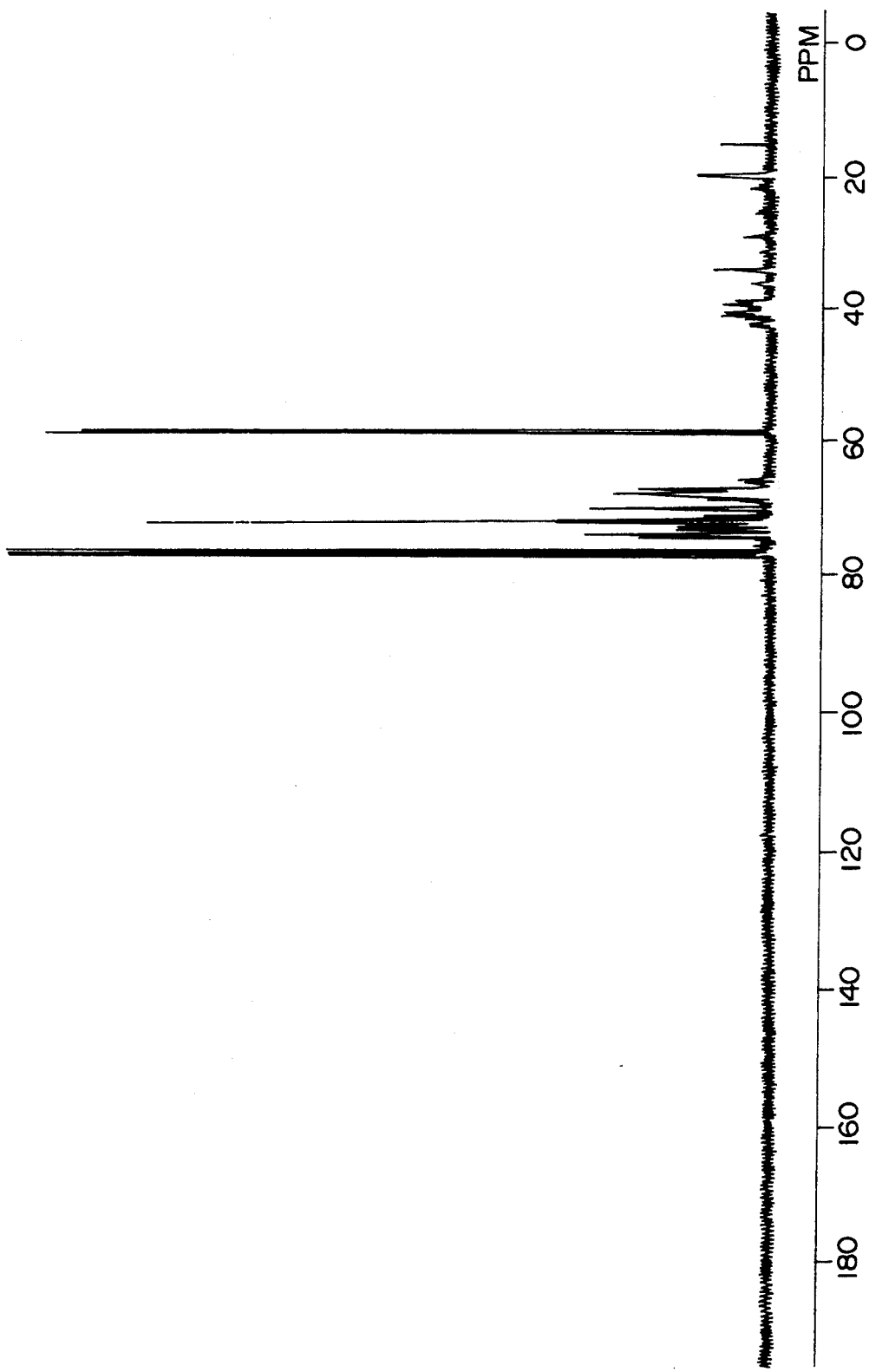

The infrared absorption spectrum is shown in FIG. 28, the $^1$H-NMR chart is shown in FIG. 29 and the $^{13}$C-NMR chart is shown in FIG. 30.

By the same reason as that described in Example 10, the polymer obtained above did not contain any of an unsaturated bond, an acetal structure and an aldehyde structure.

TABLE 1

| | kinematic viscosity (cSt) | | molecular weight | | | volume specific resistance at 80° C. ($\Omega \cdot cm$) | compatibility with Flon 134a temperature of separation at low temperature (°C.) | |
|---|---|---|---|---|---|---|---|---|
| | 40° C. | 100° C. | weight average | number average | dispersion | | 5% | 10% |
| Example 10 | 16.5 | 3.41 | 492 | 439 | 1.12 | 2.3 × 10$^{13}$ | −60.0> | −60.0> |
| Example 11 | 31.6 | 5.15 | 615 | 529 | 1.16 | 1.5 × 10$^{14}$ | −60.0> | −60.0> |
| Example 12 | 55.2 | 7.32 | 722 | 608 | 1.19 | 5.8 × 10$^{13}$ | −60.0> | −60.0> |
| Example 13 | 28.3 | 4.37 | 570 | 462 | 1.23 | 5.3 × 10$^{13}$ | −60.0> | −60.0> |
| Example 14 | 22.8 | 3.77 | 547 | 470 | 1.16 | 6.1 × 10$^{12}$ | −60.0> | −60.0> |
| Example 15 | 74.4 | 8.60 | 798 | 488 | 1.64 | 4.4 × 10$^{12}$ | −60.0> | −60.0> |
| Example 16 | 40.0 | 5.85 | 706 | 525 | 1.35 | 1.9 × 10$^{13}$ | −60.0> | −60.0> |
| Example 17 | 59.0 | 7.05 | 996 | 524 | 1.90 | 1.4 × 10$^{13}$ | insoluble | insoluble |
| Example 18 | 26.8 | 4.20 | 436 | 396 | 1.10 | 6.5 × 10$^{13}$ | −60.0> | −60.0> |
| Example 19 | 30.4 | 6.29 | — | — | — | — | −60.0> | −60.0> |

| | compatibility with Flon 134a temperature of separation at high temperature (°C.) | | after the hydrolysis test | | |
|---|---|---|---|---|---|
| | | | sample oil | | appearance of piece of copper |
| | 5% | 10% | appearance | total acid value (mg KOH/g) | |
| Example 10 | 80.0< | 80.0< | good | 0.5> | good |
| Example 11 | 80.0< | 80.0< | good | 0.5> | good |
| Example 12 | 80.0< | 80.0< | good | 0.5> | good |
| Example 13 | 80.0< | 80.0< | good | 0.5> | good |
| Example 14 | 80.0< | 80.0< | good | 0.5> | good |
| Example 15 | 80.0< | 80.0< | good | 0.5> | good |
| Example 16 | 80.0< | 80.0< | good | 0.5> | good |
| Example 17 | insoluble | insoluble | good | 0.5> | good |
| Example 18 | 80.0< | 80.0< | good | 0.5> | good |
| Example 19 | 80.0< | 80.0< | good | 0.5> | good |

What is claimed is:

1. A polyvinyl ether compound which comprises the constituting units expressed by the general formula (IX):

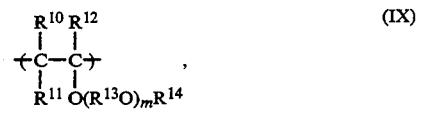

wherein $R^{10}$, $R^{11}$ and $R^{12}$ are a hydrogen atom or an alkyl group having 1 to 4 carbon atoms, respectively, and may be the same or different from each other, $R^{13}$ is an alkylene group having 2 to 4 carbon atoms, $R^{14}$ is an alkyl group having 1 to 10 carbon atoms, m is a number the average of which is in the range of 0 to 10, $R^{10}$ to $R^{14}$ may be the same or different between the constituting units and a plural of $R^{13}$O's may be the same or different from each other when the constituting unit contains a plural of $R^{13}O$'s, does not contain any of an unsaturated bond, an acetal structure and an aldehyde structure in the molecule and has a weight average molecular weight of 300 to 3000 and wherein one end of the polyvinyl ether compound has the structure expressed by the general formula (X):

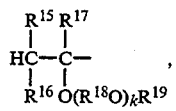
(X)

wherein $R^{15}$, $R^{16}$ and $R^{17}$ are a hydrogen atom or an alkyl group having 1 to 4 carbon atoms, respectively, and may be the same or different from each other, $R^{18}$ is an alkylene group having 2 to 4 carbon atoms, $R^{19}$ is an alkyl group having 1 to 10 carbon atoms, k is a number the average of which is in the range of 0 to 10 and a plural of $R^{18}O$'s may be the same or different from each other, and the other end has the structure expressed by the general formula (XI):

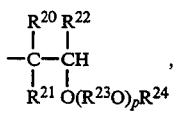
(XI)

wherein $R^{20}$, $R^{21}$ and $R^{22}$ are a hydrogen atom or an alkyl group having 1 to 4 carbon atoms, respectively, and may be the same or different from each other, $R^{23}$ is an alkylene group having 2 to 4 carbon atoms, $R^{24}$ is an alkyl group having 1 to 10 carbon atoms, p is a number the average of which is in the range of 0 to 10 and a plural of $R^{23}O$'s may be the same or different from each other.

2. A polyvinyl ether compound as claimed in claim 1, wherein the constituting units are expressed by the general formula (XII):

(XII)

wherein $R^{25}$ is an alkyl group having 1 to 4 carbon atoms and may be the same or different between the constituting units.

3. A polyvinyl ether compound as claimed in claim 1, wherein the ratio of the weight average molecular weight and the number average molecular weight is in the range of 1.05 to 2.00.

4. A polyvinyl ether compound which has the structure expressed by the general formula (XIII):

(XIII)

wherein $R^{25}$ is an alkyl group having 1 to 4 carbon atoms and may be the same or different between the constituting units expressed by the general formula (XII):

(XII)

and q is the degree of polymerization providing a weight average molecular weight of 300 to 3000.

5. A polyvinyl ether compound as claimed in claim 4, wherein the weight average molecular weight is in the range of 400 to 1,000.

* * * * *